(12) United States Patent
Baxter et al.

(10) Patent No.: US 6,187,924 B1
(45) Date of Patent: Feb. 13, 2001

(54) HYDROXAMIC AND CARBOXYLIC ACID DERIVATIVES HAVING MMP AND TNF INHIBITORY ACTIVITY

(75) Inventors: Andrew Douglas Baxter; David Alan Owen; John Gary Montana; Robert John Watson, all of Cambridge (GB)

(73) Assignee: Darwin Discovery, Ltd. (GB)

(*) Notice: Under 35 U.S.C. 154(b), the term of this patent shall be extended for 0 days.

(21) Appl. No.: 09/190,774

(22) Filed: Nov. 12, 1998

Related U.S. Application Data
(60) Provisional application No. 60/068,777, filed on Dec. 24, 1997.

(30) Foreign Application Priority Data

| Nov. 12, 1997 | (GB) | ............ 9723906 |
| Feb. 6, 1998 | (GB) | ............ 9802618 |
| Jun. 26, 1998 | (GB) | ............ 9813933 |

(51) Int. Cl.$^7$ .......... C07D 307/33; C07D 311/68; C07D 313/12; A61N 9/00; A61N 11/06; A61N 27/02; A61N 17/00
(52) U.S. Cl. ............ 544/374; 514/254.1; 514/336; 514/341; 514/348; 514/397; 514/398; 514/451; 514/534; 514/575; 546/194; 546/207; 546/210; 546/216; 546/224; 548/315.4; 548/319.5; 549/425; 560/12; 562/621; 562/622
(58) Field of Search ............ 548/316.7, 319.5, 548/315.4, 318.5; 514/397, 398, 254.1, 336, 341, 348, 451, 534; 544/207, 210, 194, 224, 266; 549/425; 560/12; 562/621, 622

(56) References Cited

U.S. PATENT DOCUMENTS

| 4,122,186 | * | 10/1978 | Lafon .................. 424/315 |
| 5,004,751 | * | 4/1991 | Mochida et al. ............ 514/390 |
| 5,554,594 | * | 9/1996 | Zoller et al. ............ 514/18 |
| 5,847,153 | * | 12/1998 | Warpehoski et al. ......... 548/319.5 |
| 5,872,152 |   | 2/1999 | Brown et al. ............ 514/575 |

FOREIGN PATENT DOCUMENTS

| 1067965 | 5/1967 | (GB) . |
| 98/29376 | 7/1998 | (WO) . |

OTHER PUBLICATIONS

Morris, J. et al. (1991) "Vinyl Sulphonyl Esters and Amides in the Synthesis of Substituted Delta–Sultams and Delta–Sultones" Journal of Organic Chemistry 56(11): 3459–3556.

Decicco, C.P. et al. (1997) "Amide Surrogates of Matrix Metalloproteinase Inhibitors: Urea and Sulphonamide Mimics" Bioorganic and Medicinal Chemistry Letters, 7(18):2331–2336.

von Bruno J.R. Nicolaus et al. (1963) "Auf das Zentralnervensystem wirkende Substanzen XXXV: Über neuartige schwefelhaltige Heterocyclen II: Synthese and Eigenschaften der 3–Alkoxy–4, 4–dialkyl–4H–1, 2–thiazet–1, 1–dioxide" Helvetica Chimica Acta vol. XLVI, Faxciculus II, No. 47.

Graafland, T. et al. (1979) "Structure an Reactivity in Tntramolecular Catalysis. Catalysis of Sulphonamide Hydrolysis by the Neighbouring Carboxyl Group" Journal of the American Chemical Society 101(23):6981–6991.

Jager, J. et al. (1984) "The Thorpe–Ingold Effect in the Intramolecular Carboxyl–Catalysed Hydrolysis of Sulphonamides" Journal of the American Chemical Society 106(1):139–143.

De Blic, A. et al. (1982) "A Convenient Facile Synthesis of Beta–Aminosulphinyl–and Beta–Aminosulphonylalkanoic Esters from Metallated Esters and N–Sulphinylamines" Synthesis 4:281–283.

Witte, Maria B., Frank J. Thornton, Teruo Kiyama et al. (1998) "Metalloproteinase inhibitors and wound healing: A novel enhancer of wound strength" *Surgery* 124(2):464–470.

Hattori, Koichi et al. (1997) "A Metalloproteinase Inhibitor Prevents Lethal Acute Graft–Versus–Host Disease in Mice" *Blood* 90(2):542–548.

* cited by examiner

*Primary Examiner*—Floyd D. Higel
(74) *Attorney, Agent, or Firm*—Saliwanchik, Lloyd & Saliwanchik

(57) ABSTRACT

Compounds of formula (I)

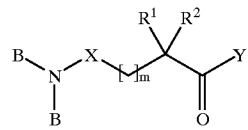

are useful as therapeutic agents, by virtue of having MMP and TNF inhibitory activity.

35 Claims, No Drawings

HYDROXAMIC AND CARBOXYLIC ACID DERIVATIVES HAVING MMP AND TNF INHIBITORY ACTIVITY

CROSS-REFERENCE TO A RELATED APPLICATION

This application claims priority from provisional application U.S. Ser. No. 60/068,777 filed Dec. 24, 1997.

FIELD OF THE INVENTION

This invention relates to hydroxamic and carboxylic acid derivatives, and to their use in medicine.

BACKGROUND OF THE INVENTION

Metalloproteinases, including matrix metalloproteinases (MMPs), (human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of the TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenases, stromelysins and gelatinases, have been shown to inhibit the release of TNF both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or THF are described in WO-A-9513289, WO-A-9611209, WO-A-96035687, WO-A-96035711, WO-A-96035712 and WO-A-96035714.

SUMMARY OF THE INVENTION

The invention encompasses compounds which are useful inhibitors of matrix metalloproteinases and/or TNFα-mediated diseases, including degenerative diseases and certain cancers. These compounds are represented by formula (I):

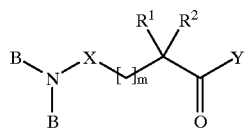

wherein
m is 0–2;
X is $S(O)_{t-2}$;
Y is OH or NHOH;
$R^1$ H or a group (optionally substituted with $R^7$) selected from $C_{1-6}$ alkyl $C_{2-4}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl and $C_{1-6}$ alkyl-cycloalkyl, and $R^2$ H or $C_{1-6}$ alkyl;

or $CR^1R^2$ is a cycloalkyl or heterocycloalkyl ring optionally substituted with $R^7$ or a group (optionally substituted with $R^7$) selected from $C_{1-6}$ alkyl, aryl, $C_{1-6}$ alkyl-aryl, heteroaryl and $C_{1-6}$ alkyl-heteroaryl;

each B is the same or different and H is or a group selected from $C_{1-6}$ alkyl-aryl, $C_{1-6}$ alkyl, cycloalkyl, $C_{1-6}$ alkyl-cycloalkyl, cycloalkenyl, heterocycloalkenyl, $C_{1-6}$ alkyl-heteroaryl, heterocycloalkyl, $C_{1-6}$ alkyl-heterocycloalkyl, aryl or heteroaryl, any of which groups is optionally substituted by a substituent selected from $R^3$, $C_{1-6}$ alkyl-$R^3$, $C_{2-6}$ alkenyl-$R^3$, aryl (optionally substituted with $R^3$), aryl-$C_{1-6}$ alkyl-$R^3$, $C_{1-6}$ alkyl-aryl (optionally substituted with $R^3$), $C_{1-6}$ alkyl-heteroaryl (optionally substituted with $R^3$), aryl-$C_{2-6}$ alkenyl-$R^5$, heteroaryl (optionally substituted with $R^3$), heteroaryl-$C_{1-6}$ alkyl-$R^3$, cycloalkyl (optionally substituted with $R^3$) and heterocycloalkyl (optionally substituted with $R^3$), provided with $NB_2$ is not $NH_2$, or B—N—B is a heterocycloalkyl ring substituted with =O or =$NOR^4$, or, when neither $R^1$ or $R^2$ is H, B—N—B is a heterocycloalkyl or heterocycloalkenyl ring optionally substituted by a substituent selected from $R^3$, $C_{1-6}$ alkyl-$R^3$, $C_{2-6}$ alkenyl-$R^3$, aryl (optionally substituted with $R^3$), aryl-$C_{1-6}$ alkyl-$R^3$, $C_{1-6}$ alkyl-aryl (optionally substituted with $R^3$), $C_{1-6}$ alkyl-heteroaryl (optionally substituted with $R^3$), aryl-$C_{2-6}$ alkenyl-$R^5$, heteroaryl (optionally substituted with $R^3$), heteroaryl-$C_{1-6}$ alkyl-$R^3$, cycloalkyl (optionally substituted with $R^3$), and heterocycloalkyl (optionally substituted with $R^3$);

$R^3$ is $C_{1-6}$ alkyl, $C_{2-6}$ alkenyl-$R^5$, halogen, CN, $NO_2$, $N(R^4)_2$, $OR^4$, $C(=NOR^6)R^4$, $CON(R^4)_2$, $COR^4$, $CO_2R^8$, $NR^4R^5$, $S(O)_{0-2}N(R^4)_2$;

$R^4$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$ or $NO_2$, and for each case of $N(R^4)_2$ the $R^4$ groups are the same or different or $N(R^4)_2$ is heterocycloalkyl optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$ or $NO_2$;

$R^5$ is $COR^4$, $CON(R^4)_2$, $CO_2R^6$ or $SO_2R^6$;

$R^6$ is $C_{1-6}$ alkyl, aryl, $C_{1-6}$ alkyl-aryl, heteroaryl or $C_{1-6}$ alkyl-heteroaryl; and $R^7$ is $OR^4$, $COR^4$, $CO_2R^8$, $CON(R^4)_2$, $NR^4R^5$, $S(O)_{0-2}R^6$, $SO_2N(R^4)_2$, halogen, CN or cycloimidyl (optionally substituted with $R^8$); and $R^8$ is H or $C_{1-6}$ alkyl;

and the salts, solvates, hydrates, N-oxides, protected amino, protected carboxy, or protected hydroxamic acid derivatives thereof.

Compounds of formula (I) are disclosed for the first time as having therapeutic utility. Compounds of formula (I) are new, except those wherein Y is OH and $CR^1R^2$ is $CH_2$ or $NB_2$ is $NH_2$, $N(Ph)H$, $N(Ph)CH_3$, $N(C_6HG_{11})CH_3$ or N(4-methoxybenzoyl)$_2$.

Combinations of substituents and/or variables are only permissible if such combinations result in stable compounds.

DESCRIPTION OF THE INVENTION

Preferred compounds of the invention are those wherein any one or more of the following apply:

X is $SO_2$;

B is not H;

B is optionally substituted $C_{1-6}$ alkyl, cycloalkyl, heterocycloalkyl, $C_{1-6}$ alkyl-aryl or $C_{1-6}$ alkyl-heteroaryl;

B—N—B is an optionally substituted heterocycloalkyl ring;

B—N—B is a heterocycloalkyl ring substituted with =$NOR^4$;

$R^1$ is optionally substituted $C_{1-6}$ alkyl, $C_{1-6}$ alkyl-heteroaryl, $C_{1-6}$ alkyl-aryl or $C_{1-6}$ alkyl-heterocycloalkyl;

$CR^1R^2$ is the said optionally substituted cycloalkyl or heterocycloalkyl ring;

$R^3$ is $C_{1-6}$ alkyl, $C_{2-6}$ alkenyl-$R^5$, halogen, CN, $NO_2$, $N(R^4)_2$, $OR^4$, $COR^4$, $NR^4R^5$, $S(O)_{0-2}R^6$ or $SO_2N(R^4)_2$; and $R^7$ is $CON(R^4)_2$, $NR^4R^5$, $SO_2N(R^4)_2$ or cycloimidyl.

It will be appreciated that the compounds according to the invention can contain one or more asymmetrically substituted carbon and sulfur atoms. The presence of one or more of these asymmetric centres in a compound of formula (I) can give rise to stereoisomers, and in each case the invention is to be understood to extend to all such stereoisomers, including enantiomners and diastereomers, and mixtures including racemic mixtures thereof.

It will further be appreciated that the compounds according to the invention may contain an oxime. This oxime can give rise to geometrical isomers, and in each case the invention is to be understood to extend to all such isomers and mixtures thereof.

As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cycloalkyl" refers to a saturated alicyclic moiety having from three to six carbon atoms and which is optionally benzofused at any available position. This term includes for example cyclopropyl, cyclobutyl, cyclopentyl, cyclohexyl, indanyl and tetrahydronaphthyl.

The term "heterocycloalkyl" refers to a saturated heterocyclic moiety having from three to six carbon atoms and one or more heteroatoms selected from N, O, S and oxidised verisons thereof, and which is optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having from three to six carbon atoms and having in addition one double bond. This term includes, for example, cyclopentyl and cyclohexenyl.

The term "heterocycloalkenyl" refers to an alicyclic moiety having from three to six carbon atoms and one or more heteroatoms selected from N, O, S and oxidised versions thereof, and having in addition one double bond. This term includes, for example, dihydropyranyl.

The term "aryl" refers to an aromatic carbocyclic radical having a single ring or two considered rings This term includes, for example phenyl or naphthyl.

The term "heteroaryl" refers to aromatic ring systems of five to ten atoms of which at least one atom is selected from O, N and S, and includes, for example, furanyl, thiophenyl, pyridyl, indolyl, quinolyl and the like.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "benzofused" refers to the addition of a benzene ring sharing a common bond with the defined ring system.

The term "optionally substituted" means optionally substituted with one or more of the groups specified, at any available position or positions.

The term "halogen" means fluorine, chlorine, bromine or iodine.

The term "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimide or like group. A carboxyl group can be protected in the form of an ester such as the methyl, ethyl, benzyl or tert-butyl ester. A hydroxamic acid may be protected as either N or O-substituted derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^9$ where $R^9$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, B, X and Y are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises acylating an amine of formula $B_2NH$ (II) with an acylating agent formula $Z-X-(CH_2)_m-CR^1R^2-COY$ (III) wherein Z represents a suitable leaving group (e.g. a halogen such as bromine), and Y is OH or NHOH or a protected form thereof. This reaction may be performed in an inert solvent such as tetrahydrofuran, in the presence of an organic or inorganic base.

Acylating agents of formula (III) where $X=SO_2$ may be prepared from $R^{10}S-CH_2)_m-CR^1R^2-COY$ (IV), where $R^{10}$ is H or a suitable labile group such as acetyl, by treatment with chlorine in an appropriate solvent such as water at an appropriate temperature such as 0° C. Acylating agents of formula (III) where X=SO may also be prepared from compound (IV) by treatment with $SO_2CL_2$ and acetic anhydride in an appropriate solvent such as dichloromethane at an appropriate temperature such as 0° C.

Sulfanyl compounds of formula (IV) are readily prepared by alkylation of a compound $R^{10}SH$ with an alkylating agent of the form $Z^A-(CH_2)_m-CR^1R^2-COY$ (V), where $Z^A$ is a leaving group (e.g. a halogen such as bromine, or an alkylsulfonate ester such as methanesulfonate). Many compounds of formula (V) are available commercially, or may be prepared by standard chemistry known to those skilled in the art from materials available commercially.

Compounds of formula (V) where m=1 may be prepared from compounds of formula $HOCH_2CR^1R^2COY$ (VI). Thus, for example, a compound of formula (V) where $Z^A$ is methanesulfonate may be prepared by treatment of a compound of formula (VI) with methanesulfonyl chloride in the presence of an organic base such as triethylamnine in an inert solvent such as dichloromethane.

Compounds of formula (VI) may be prepared by the reduction of compounds of formula $R^{11}O_2CCR^1R^2COY$ (VII), where $COOR^{11}$ represents a suitable ester, e.g. an ethyl ester. Suitable conditions for the reduction comprise the use of diisobutylaluminium hydride is toluene at –40° C.

Compounds of formula (VII) may be prepared by the sequential alkylation of, for example, diethyl malonate, with alkylating agents of formula $R^1-Z^A$(VIII) and $R^2-Z^A$(IX), wherein $Z^A$ is as defined above, followed by hydrolysis under basic conditions. Many alkylating agents of formula (VIII) or (IX) are available commercially or may be prepared from materials available commercially by methods known to those skilled in the art.

Compounds of formula (IV) where m=1 and $R^2=H$ may also be prepared by the reaction of a compound $R^{10}SH$ with an acrylate of the form $H_2C=CR^1CO_2H$ (X). Compounds of formula (X) may be prepared by the Mannich reaction (i.e. with paraformaldehyde and piperidine in a suitable organic solvent, such as 1,4-dioxane) on a dicarboxylic acid of general formula $HO_2C-CHR^1-CO_2H$ (XI). This reaction involves an eliminative decarboxylation step, resulting in the formation of an α,β-unsaturated carboxylic acid (i.e. where Y=OH) directly.

Dicarboylic acids of formula (XI) may be prepared by the alkylation of, for instance, diethyl malonate with an alkylating agent of formula $R^1-Z^A$ (VIII), wherein $Z^A$ is as defined above, followed by hydrolysis under basic conditions.

Amines of the structure depicted in formula (II) are commercially available or may be prepared by standard aromatic, heteroaromatic or other chemistry known to those skilled in the art, from materials available commercially.

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol, e.g. ethanol) of a compound of formula (I) wherein $R^1$ is $C_{2-6}$ alkenyl group. Similarly, a compound of formula (I) where $X=SO_2$ may be prepared from a compound of formula (I) where X=SO by oxidation with, for example sodium periodate and ruthenium chloride trihydrate is an appropriate solvent, for example acetronile-tetrachloromethane-water. Acids of general formula (I) (Y=OH) may be converted to hydroxamic acids (Y=NHOH) using methods known to those skilled in the art.

Any mixtures of final products of intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysins, collagenases and gelatinases. Compounds according to the invention may also exhibit in vitro inhibition of membrane shedding events known to be mediated by metalloproteinases, for example, TNF release, TNF receptor shedding IL-6 receptor shedding, IL-1 receptor shedding, CD23 shedding and L-selectin shedding. The activity and selectivity of the compounds may be determined by use of the appropriate enzyme inhibition test, for example as described in Examples A–M of WO 98/05635, or by the following assay for the inhibition of CD23 shedding.

The potency of compounds of general formula (I) to act as inhibitors of the shedding CD23 is determined using the following procedure: a 100 $\mu$M solution of the compound being tested, or dilutions thereof, is incubated at 37° C. in an atmosphere of 5% $CO_2$ with RPMI 8866 cells, which shed CD23 spontaneously without stimulation. After 1 h, the cells are removed by centrifugation and the supernatant assayed for levels of sCD23 using an ELISA kit available commercially. The activity in the presence of 0.1 mM inhibitor, or dilutions thereof, is compared to activity in a control devoid of inhibitor and the results reported as that inhibitor concentration effecting 50% inhibition of the shedding of CD23.

This invention also relates to a method of treatment for patients (including man and/or mammalian animals raised in the diary, meat or fur industries or as pets) suffering from disorders or diseases which can be attributed to MMPs as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bond resorption, haemorrhage, coagulation, acute phase response, cachexia and anorexia, acute infections, HIV infections, fever, shock states, graft versus host reactions, dermatogological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis and aspirin-independent anti-thrombosis.

Compounds of formula (I) may also be useful in the treatment of pelvic inflammatory disease (PID), age-related muscular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

For the treatment of rheumatoid arthritis, osteoarthritis, and in diseases and indications resulting from the over-expression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tables for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters wit ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparing may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipients which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouth washes and gargles.

Dosage levels of the order of from about 0.05 mg to about 140 mg per kilogram of body weight per day are useful in the treatment of the above- indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depended upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

In the Examples, the following abbreviations are used:

| | |
|---|---|
| TNFα | Tumour Necrosis Factor α |
| LPS | Lipopolysaccharide |
| ELISA | Enzyme-linked immunosorbent assay |
| EDC | 1-Ethyl-2-dimethylaminopropylcarbodiimide |
| RT | Room Temperature |

Intermediate 1

3-Iodo-1-(3,4,5-trimethyl-2,5-dioxoimidazolidin-1-yl)-propane

Sodium hydride (2.2 g) was added to a solution of 3,4,4-trimethylhydantoin (7.1 g) in dimethylformamide (50 ml) at room temperature and the mixture was stirred for 1 h. 3-Chloro-1-bromopropane (4.9 ml) was then added and the solution was stirred overnight. The mixture was then poured into water (300 ml) and extracted with diethyl ether, the ether layer was then dried ($MgSO_4$) and evaporated and the residue was dissolved in acetone (100 ml) to which was added sodium iodide (10 g). The mixture was heated at reflux for 18 h, then evaporated and the residue was dissolved in diethyl ether and washed with water, then dried ($MgSO_4$) and evaporated to give the title compound (11 g, 70%) as a brown oil.

$R_f$ 0.85 (diethyl ether)

Intermediate 2

Dibenzyl (3-(3,4,4-Trimethyl-2,5-dioxoimidazolidin-1-yl)-propyl)malonate

A solution of dibenzyl malonate (5.7 g) in anhydrous tetrahydrofuran (200 ml) was treated at 0° C. with sodium hydride (60% dispersion in mineral oil, 3.1 g). The mixture was allowed to warm to room temperature and stirred for 30 minutes under nitrogen. The mixture was than treated with a solution of intermediate 1 (6.2 g) in tetrahydrofuran (100 ml) and heated at reflux for 12 hours. The reaction was then cooled, filtered, and the filtrate evaporated in vacuo. The residue was partitioned between ethyl acetate (200 ml) and saturated aqueous ammonium chloride (150 ml). The organic layer was washed with water (100 ml), brine (100 ml), dried ($MgSO_4$), filtered and the filtrate evaporated in vacuo. The residue was purified by column chromatography on silica gel eluting with 20% ethyl acetate in hexane to yield the title compound (7.1 g, 80%) as a colourless oil.

$R_f$ 0.53 (diethyl ether)

Intermediate 3

2-Methylene-5-(3,4,4-trimethyl-2,5-dioxoimidazolidin-1-yl)-pentanoic Acid

A solution of intermediate 2 (10 g) in dioxane (200 ml) was treated with 10% palladium on charcoal (1.7 g) and hydrogenated at atmospheric pressure until the hydrogen uptake had ceased. The catalyst was removed by filtration through Celite® and the filtrate treated with piperdine (3.2 g) at room temperature. After 30 minutes the reaction was treated with formaldehyde (37% solution in water; 15 ml), stirred for two hours at room temperature and then heated at 80° C. for two hours. The mixture was cooled, the solvent removed in vacuo and the residue partitioned between ethyl acetate (200 ml) and 10% aqueous citric acid (100 ml). The organic layer was washed with water (100 ml), brine (100 ml), dried over magnesium sulfate, and filtered, and the filtrate evaporated in vacuo. The residue was purified by column chromatography on silica gel eluting with 40% ethyl acetate in hexane to yield the title compound (5.40 g, 95%) as a colourless oil.

$R_f$ 0.4 (ethyl acetate)

Intermediate 4

2-Methylene-3-methylbutanoic acid

Morpholine (39.4 g) was added to a solution of isopropylmalonic acid (60.1 g) in water (300 ml) and acetic acid (47 ml). The mixture was stirred for 20 min, then a solution of aqueous formaldehyde (37% aq, 18.54 g) was added. The mixture was stirred at room temperature overnight, then heated at 80° C. for 2 h and recooled to room temperature. The mixture was filtered, basified with sodium bicarbonate and washed with dichloromethane (100 ml). The pH was adjusted to 4 with dilute HCl, then the mixture was extracted with dichloromethane (3×200 ml), the organic extracts were combined and washed with water and brine, dried (MgSO$_4$) and then evaporated to give the title compound as colourless oil (32 g).

R$_f$0.45 (EtOAc).

Intermediate 5

2-Bromomethyl-5-(3,4,4-trimethyl-2,5-dioxoimidazolidin-1-yl)-pentanoic Acid

Intermediate 3 (5.4 g) was treated with 45% hydrogen bromide in acetic acid (50 ml) at room temperature. After three hours the solution was poured into water (300 ml) and the product extracted with ethyl acetate (3×100 ml). The organic extracts were combined, washed with water (100 ml), brine (100 ml), dried over magnesium sulfate, and filtered, and the filtrate evaporated in vacuo. The residue was dried by azeotrope with toluene (2×10 ml) to yield the title compound (4.0 g, 56%) as a viscous oil.

R$_f$0.35 (ethyl acetate)

Similarly prepared was

Intermediate 6

2-Bromomethyl-3-methylbutanoic Acid

From intermediate 4 (32 g), as colourless liquid (52.3 g).

R$_f$0.43 (EtOAc).

Intermediate 7

Methyl-2-Bromomethyl-5(3,4,4-trimethyl-2,5-dioxoimidazolidin-1-yl)pentanoate

Acetyl chloride (15 ml) was was added to ice cold methanol (200 ml) dropwise over 20 min, then a solution of intermediate 5 (3.5 g) in methanol (20 ml) was added and the solution was stirred at room temperature for 3 h. The mixture was then evaporated in vacuo and the residue dissolved in dichloromethane )100 ml) and washed with saturated sodium bicarbonate solution and brine. The solvent was dried and evaporated to give the title compound (2.05 g) as pale yellow oil.

R$_f$0.65 (ether).

Intermediate 8 tert-Butyl-2-Bromomethyl-5-(3,4,4-trimethyl-2,5-dioxoimidazolidin-1-yl)pentanoate Isobutylene (100 ml) was added to a solution of the intermediate 5 (36.1 g) and sulfuric acid (1.2 ml) in dichloromethane (110 ml) at −78° C. in a Parr pressure reactor. The vessel was sealed and the mixture stirred at room temperature for 24 h, then cooled to −5° C. and the solution was removed and washed with saturated sodium carbonate and water, then dried (MgSO$_4$) and evaporated to give the title compound as a colourless oil (35.9 g).

R$_f$0.73 (ether).

Similarity prepared was

Intermediate 9 tert-Butyl-2-Bromomethyl-3-methylbutanoate

From intermediate 6 (52.3 g), as colourless liquid (64.0 g).

R$_f$0.72 (EtOAc).

Intermediate 10

Methyl 2-Acetylsulfanylmethyl-5-(3,4,4-trimethyl-2,5-dioxoimidazolidin-1-yl)pentanoate Potassium thiolacetate (1.2 g) was added to a solution of intermediate 7 (1.5 g) in dimethylformamide (20 ml) at room temperature and the mixture was then heated at 100° C. for 3 h. The mixture was added to water and extracted with ether (3×50 ml). The solvent was washed with sodium bicarbonate solution, water and brine, the dried (MgSO$_4$) and evaporated to give a brown oil. This was purified by silica gel column chromatography, eluting with ether, to give the title compound (1.2 g) as an amber oil.

R$_f$0.55 (ether)

Similarly prepared were:

Intermediate 11 tert-Butyl 2-Acetylsulfanylmethyl-5-(3,4,4-trimethyl-2,5-dioxoimidazolidin-1-yl)pentanoate From intermediate 8 (35.9 g), as a yellow oil (34.5 g).

R$_f$0.66 (ether).

Intermediate 12 tert-Butyl 2-Acetylsulfanylmethyl-3-methylbutanoate

From intermediate 9 (64 g) as colourless oil (55.7 g).

R$_f$0.68 (EtOAc).

Intermediate 13

Methyl 2-(Chlorosulfonylmethyl)-5-(3,4,4-trimethyl-2,5-dioxoimidazolidin-1-yl)pentanoate Chlorine gas was bubbled through a suspension of intermediate 10 (1.2 g) in 5% aqueous acetic acid (50 ml) at 0° C. for 20 min. The suspension was stirred for 20 min, then placed under vacuum to remove excess chlorine for 5 min. The suspension was then extracted with dichloromethane (2×50 ml) and the solvent washed with water and brine. The organic layer was dried over magnesium sulfate and evaporated to give the title compound (1.10 g) as pale yellow oil, which slowly crystallised on standing.

R$_f$0.45 (ether).

Similarly prepared were:

Intermediate 14 tert-Butyl 2-Chlorosulfonylmethyl-5-(3,4,4-trimethyl-2,5-dioxo-imidazolidin-1yl)pentanoate From intermediate 11 (1.04 g) as a viscous pale yellow oil (0.86 g).

R$_f$0.48 (ether).

Intermediate 15 tert-Butyl 2-Chlorosulfonylmethyl-3-methylbutanoate

From intermediate 12 (50 g) as pale yellow oil (49.9 g).

R$_f$0.54 (EtOAc).

Intermediate 16

N-Methyl-2-phenoxyethylamine

This compound was prepared according to the method described by Grieco and Bahsas (*J. Org. Chem.*, 1987, 52, 5747–5749) from 2-phenoxyethylamine (1.00 g), as a near colourless oil (0.88 g, 81%).

$R_f$ 0.32 (94:5:1 dichloromethane/methanol/ammonium hydroxide).

Intermediate 17

2-Hydroxymethylbenzofuran

To a stirred solution of benzofuran 2-carboxylic acid (2.50 g) in tetrahydrofuran (50 ml) at 0° C. under nitrogen was added a solution of lithium aluminium hydride (1.0M; 7.7 ml) in tetrahydrofuran. Stirring was continued for 2 h, allowing the temperature to rise to RT. The mixture was diluted with diethyl ether (50 ml) and quenched with water (30 ml). The aqueous layer was separated and extracted with diethyl ether (2×25 ml). The combined extracts were washed with water (30 ml), sodium hydroxide solution (1M; 30 ml), water (30 ml), brine (30 ml) and dried ($MgSO_4$). Filtration and evaporation of solvent under reduced pressure yielded the title compound (1.11 g, 49%) as a colourless oil.

$R_f$ 0.29 (2:1 hexane/ethyl acetate).

Intermediate 18

2-Chloromethylbenzofuran

To a stirred solution of intermediate 17 (1.10 g) in dichloromethane (50 ml) at RT was added pyridine (646 mg) and 4-toluenesulfonyl chloride (1.56 g). Stirring was continued for 72 h at RT and a further 24 h at reflux. The cooled solution was diluted with dichloromethane (50 ml) and washed with dilute hydrochloric acid (1M; 25 ml), water (2×25 ml), brine (25 ml) and dried ($MgSO_4$). Filtration and evaporation of solvents under reduced pressure and purification of the residue by silica gel column chromatography, eluting with 5:1 hexane/ethyl acetate, yielded the title compound (337 mg, 27%) as a colourless oil.

$R_f$ 0.49 (2:1 hexane/ethyl acetate).

Intermediate 19

N-Methyl Benzofuran-2-yl methylamine

This compound was prepared according to the method of Butera et al (*J. Med. Chem.*, 1991, 34, 3212–3228) from intermediate 18 (330 mg), as a near colourless oil (883 mg, 8%).

$R_f$ 0.30 (9:1 dichloromethane/methanol)

Intermediate 20

Diethyl Tetrahydropyran-4,4-dicarboxylate

Diethyl malonate (32.0 g) was added to a solution of sodium ethoxide (1 equivalent) in ethanol and the solution was stirred for 30 min. 2-Bromoethylether (46.0 g) was then added and the mixture was stirred at reflux for 3 h. The mixture was then cooled, evaporated in vacuo and the residue partitioned between water and dichloromethane. The organic layer was separated and washed with water and brine, then dried ($MgSO_4$) and evaporated. The residue was then purified by flash column chromatography on silica gel, eluting with 4:1 hexanes/ether, to give the title compound (28.0 g) as colourless liquid.

$R_f$ 0.33 (4:1 hexanes/ether).

Intermediate 21

Ethyl 4-Hydroxymethyltetrahydropyran-4-carboxylate

A solution of di-isobutylaluminium hydride in toluene (82 mmol) was added to a solution of intermediate 20 (9.5 g) in toluene at −40° C. over 30 min. The mixture was stirred for 1 h, then ethanol (100 ml) was added dropwise over 30 min. Sodium borohydride (2.0 g) was then added in small portions over 20 min, and the mixture stirred for 1 h. Saturated sodium sulfate (100 ml) was then added dropwise followed by ethyl acetate (200 ml). The mixture was vigorously stirred for 1 h, then filtered through Celite and the filtrate evaporated to give the title compound (5.6 g) as colourless liquid.

$R_f$ 0.60 (EtOAc).

Intermediate 22

Ethyl 4-(Methanesulfonyloxy) methyltetrahydropyran-4-carboxylate

Methanesulfonyl chloride (4.6 ml) was added to a solution of intermediate 21 (11.0 g) at 0° C. in dichloromethane (30 ml), followed by triethylamine (8.0 ml). The mixture was stirred for 1 h, then washed with citric acid (5% aq, 30 ml), saturated sodium bicarbonate and brine. The organic layer was separated, and then dried ($MgSO_4$) and evaporated to give the title compound as colourless oil (15.2 g).

$R_f$ 0.65 (ether).

Intermediate 23

Ethyl 4-(Acetylsulfanylmethyl)tetrahydropyran-4-carboxylate

A solution of intermediate 22 (16.0 g), sodium iodide (0.2 g) and potassium thioacetate (12.0 g) in dimethylformamide (100 ml) was heated at 80° C. for 6 h. The resulting black viscous mixture was then added to aqueous bicarbonate (300 ml) and extracted with ether. The ether layer was washed with water and brine, then dried ($MgSO_4$) and evaporated. The residue was purified by flash column chromaotography on silica gel, eluting with 1:1 ether/hexanes, to give the title compound (6.5 g) as pale yellow oil.

$R_f$ 0.45 (1:1 ether/hexanes)

Intermediate 24

Ethyl 4-(chlorosulfonyl)methyltetrahydropyran-4-carboxylate

Chlorine gas was bubbled through a suspension of intermediate 23 (3.2 g) in water (100 ml) and acetic acid (5 ml) at 0° C. for 30 min. The yellow suspension was stirred at the same temperature for 30 min, then partially evaporated under vacuum and the aqueous residue extracted with dichloromethane (100 ml). The combined organic extracts were washed with iced-cold water and brine, then dried ($MgSO_4$) and evaporated to give the title compound (3.3 g) as colourless solid.

$R_f$ 0.45 (ether).

Intermediate 25

2-(4-Chlorophenoxy)-2,2-dimethylpropionyl Chloride

To a stirred solution of 2-(4-chlorophenoxy)-2,2-dimethylpropionic acid (5.00 g) in dichloromethane (100 ml) and dimethylformamide (2 drops) at 0° C. under nitrogen was added oxalyl chloride (14.8 g). The mixture was stirred overnight with the temperature rising to RT. The mixture was evaporated under reduced pressure to dryness to yield the title compound (5.26 g, 97%) as a brown liquid.

$R_f$ 0.65 (5:1 hexane/ethyl acetate).

Intermediate 26

2-(4-Chlorophenoxy)-2,2-dimethylpropionic Acid N-Methyl Amide

To a stirred 40% aqueous solution of methylamine (20 ml) at 0° C. was added intermediate 25 (1.00 g). The mixture was stirred for 30 mins and then the resulting precipitate was collected by filtration and dried in vacuo to yield the title compound (576 mg, 59%) as a white solid.

$R_f$ 0.47 (2:1 ethyl acetate/hexane).

Intermediate 27

N-[2-(4-chlorophenoxy)-2,2-dimethylpropyl]-N-methylamine

To a stirred solution of intermediate 26 (300 mg) in tetrahydrofuran (10 ml) at 0° C. under nitrogen was added a solution of borane-dimethyl sulphide in tetrahydrofuran (2M, 1 ml). The mixture was heated at reflux for 4 h then cooled and diluted with water (30 ml). The mixture was extracted with dichloromethane (3×20 ml) and the combined extracts were washed with water (2×20 ml), brine (20 ml) and dried (MgSO$_4$). Filtration and evaporation of solvents in vacuo yielded a colourless oil. To a stirred solution of the oil in methanol (20 ml) at RT was added concentrated hydrochloric acid (3 ml). The mixture was stirred for 2.5 h then diluted with water (80 ml) and washed with hexane (2×20 ml). The aqueous mixture was basified (2M NaOH; pH 12) and extracted with dichloromethane (5×20 ml). The combined organic fractions were washed with water (2×20 ml), brine (20 ml) and dried (Mg SO$_4$). Filtration and evaporation of solvents in vacuo yielded the title compound (146 mg, 58%) as a colourless oil.

$R_f$ 0.32 (94:5:1 dichloromethane/methanol/ammonium hydroxide).

Intermediate 28

N-(tert-Butyloxycarbonyl)-4-piperidinol

Was prepared according to the method of K. M. Wells et al (*Tetrahedron Lett.*, 1996, 37(36), 6439–6442) as a pale yellow solid (46.5 g, 99%)

$R_f$ 0.67 (EtOAc)

Intermediate 29

4-(Piperidin-4-yloxy)pyridine, Bis(trifluoroacetate)

Sodium hydride (1.8 g) was added to a solution of intermediate 28 (3.4 g) in dimethylformamide (15 ml), cooled in ice, and held under nitrogen. The suspension was then stirred at room temperature for 1 h, treated with 4-chloropyridine hydrochloride (2.7 g), and heated to 100° C. for a further 2 h. After cooling, the mixture was partitioned between diethyl ether (100 ml) and water (100 ml). The organic phase was collected, washed with water (20 ml), saturated brine (20 ml), dried (Na$_2$SO$_4$) and evaporated to dryness in vacuo. The beige solid residue was recrystallised from diethyl ether to provide the intermediate ether as a crystalline pale brown solid (4.24 g). The recrystallised solid was then dissolved in dichloromethane (80 ml), treated with trifluoroacetic acid (20 ml), and stirred at room temperature for 16 h. The mixture was then concentrated under reduced pressure and co-evaporated with 50% dichloromethane/hexane (20 ml) to provide the title compound as a beige solid (4.8 g, 70%).

$R_f$ 0.11 (8% methanol/dichloromethane with trace triethylamine)

Similarly prepared were:

Intermediate 30

4-(4-Cyanophenyloxy)piperidine, Trifluoroacetate

From intermediate 28 (3.0 g) and 4-fluorobenzonitrile (1.95 g), as a colourless solid (1.34 g, 28%)

Rf$_{0.1}$ (50% hexane and 0.1% AcOH in EtOAc)

Intermediate 31

4-(4-Chlorophenyloxy)piperidine, Hydrochloride

Sodium hydride, as a 60% dispersion in mineral oil (2.11 g) was added to a solution of intermediate 28 (10.0 g) in anhydrous dimethylsulfoxide (200 ml). After stirring for 30 min at RT under nitrogen, potassium benzoate (8.56 g) was added, followed, after 20 min, by 1-chloro-4-fluorobenzene (6.90 g). The mixture was heated at 60° C. for 2 h, then cooled to RT and diluted with water (600 ml) and the pH adjusted to 5. The solution was washed with hexane (100 ml), basified to pH 11, then extracted with ethyl acetate (3×100 ml). The combined ethyl acetate extracts were washed with saturated aqueous brine (50 ml), dried over sodium sulfate and evaporated, and then the residue was crystallised from hexane. The crystalline solid obtained was dissolved in a mixture of ethanol and dioxane (1:1, 150 ml) and saturated with hydrogen chloride gas. After 2 h at RT, the solution was purged with nitrogen gas and then concentrated under reduced pressure. The residue was dissolved in a minimum amount of methanol, and then diluted with ether. The precipitate which formed was collected by filtration and dried to give the title product (5.36 g, 41%) as a colourless solid.

$R_f$ 0.35 (8% MeOH/dichloromethane)

Intermediate 32

N-(tert-Butoxycarbonyl)-4-piperidone

This compounds was prepared according to the method of I. M. Labouta et al, *Eur. J. Med. Chem. Chim. Ther.*, 1982, 17, 531–535, as a colourless solid (9.72 g, 98%).

Intermediate 33 tert-Butyl-4-Hydroxyiminopiperidine-1-carboxylate

Hydroxylamine hydrochloride (2.95 g), sodium acetate (3.80 g) and intermediate 32 (7.70 g) were combined in ethanol (40 ml) and stirred at room temperature for 72 h. Water (100 ml) was added, and the mixture extracted with diethyl ether (2×50 ml). The combined organic extracts were washed with saturated sodium bicarbonate (2×30 ml), water (30 ml), saturated brine (30 ml), dried (MgSO$_4$) and concentrated in vacuo to provide the title compound (7.94 g, 96%) as a pale yellow solid.

$R_f$ 0.30 (2% methanol/dichloromethane with trace triethylamine)

Intermediate 34 tert-Butyl 4-(4-Cyanophenoxyimino)piperidine-1-carboxylate

Sodium hydride, as a 60% dispersion in mineral oil (0.103 g), was added to a solution of intermediate 33 (0.50 g) in anhydrous tetrahydrofuran (30 ml), and the mixture stirred under nitrogen at room temperature. After 30 min, 4-fluorobenzonitrile was added as a solution in dry tetrahydrofuran (3 ml), and the mixture stirred for a further 24 h at room temperature. The solvents were then removed in vacuo, the residue azeotroped twice with toluene before purification by silica gel column chromatography, with 2% methanol/dichloromethane as eluent, to provide the title compound (0.57 g, 78%) as a pale yellow solid.

$R_f$ 0.63 (2% methanol/dichloromethane with trace triethylamine)

Similarly prepared was:

Intermediate 35 tert-Butyl 4-(4-Chlorobenzyloxyimino)piperidine-1-carboxylate

From intermediate 33 (0.80 g) and 4-chlorobenzyl bromide, as a colourless solid (0.54 g, 43%) after purification by silica gel column chromatography with 7% diethyl ether/dichloromethane as eluent.

$R_f$ 0.50 (7% diethyl ether/dichloromethane)

Intermediate 36

4-(4-Cyanophenoxyimino)piperidine, Trifluoroacetate Salt

Trifluoroacetic acid (1 ml) was added to a solution of intermediate 34 (0.56 g) in dichloromethane (9 ml). After stirring for 6 h at room temperature, the solvents were removed in vacuo. The residue was dissolved in dichloromethane (1 ml) and diluted with diethyl ether to induce crystallisation. The mixture was cooled, filtered and washed with diethyl ether to furnish the title compound (0.56 g, 96%) as a off-white solid.

$R_f$ 0.28 (8% methanol/dichloromethane with trace triethylamine)

Similarly prepared was:

Intermediate 37

4-(4-chlorobenzyloxyimino)piperidine, Trifluoroacetate Salt

From intermediate 35 (0.54 g), as a white solid (0.49 g, 87%).

$R_f$ 0.15 (3% methanol/dichloromethane with trace triethylamine)

EXAMPLE 1

Methyl 2-((2-Phenoxyethylsulamoyl)methyl)-5-(3,4,4-trimethyl-2,5-dioxoimidazolidin-1-yl)pentanoate To a stirred solution of intermediate 13 (500 mg) in dichloromethane (25 ml) at 0° C. were added 2-phenoxyethylamine (186 mg) and triethylamine (137 mg). Stirring was continued for 18 h, with the temperature rising to RT. The reaction mixture was diluted with dichloromethane (50 ml) and washed with water (2×20 ml), hydrochloric acid (1M; 20 ml), water (20 ml), brine (20 ml) and then dried ($MgSO_4$). Filtration and evaporation of solvents in vacuo yielded the title compound (581 mg, 91%) as a colourless oil.

$R_f$ 0.31 (3:1 ethyl acetate/hexane)
MS 467 ($M^+$)

Similarly prepared were:

EXAMPLE 2

Methyl 2-((N-Methyl-(2-phenoxyethyl)sulfamoyl)methyl)-5-(3,4,4-trimethyl-2,5-dioxoimidazolidin-1-yl)pentanoate From intermediate 16 (328 mg) and intermediate 13 (800 mg) as a colourless oil (874 mg, 83%).

$R_f$ 0.27 (3:1 ethyl acetate/hexane)
MS 484 ($M^+$)

EXAMPLE 3

Methyl 2-((N-Methyl-(2-(4-Chlorophenoxy)ethyl)sulfamoyl)methyl)-5-(3,4,4-trimethyl-2,5-dioxoimidazolidin-1-yl) pentanoate From 2-(4-chlorophenoxy)-N-methylethylamine (416 mg) and intermediate 13 (827 mg) as a colourless oil (955 mg, 82%).

$R_f$ 0.35 (3:1 ethyl acetate/hexane).
MS 518 ($M^+$)

EXAMPLE 4 tert-Butyl 2-((N-Methyl-(benzofuran-2-yl)methylsulfamoyl)methyl)-5-(3,4,4-trimethyl-2,5-dioxoimidazolidin-1-yl) pentanoate From intermediate 19 (180 mg) and intermediate 14 (459 mg) as a colourless oil (589 mg, 98%).

$R_f$ 0.44 (2:1 ethyl acetate/hexane)
MS 536 ($M^+$)

EXAMPLE 5

Ethyl 4-(4-(4-Chlorophenyl)piperazin-1-yl) sulfonylmethyl)tetrahydropyran-4-carboxylate 4-Chlorophenylpiperazine dihydrochloride (7.3 g) and triethylamine (12 ml) were stirred in dichloromethane for 10 min, then the mixture was cooled in ice and a solution of intermediate 24 (6.9 g) in dichloromethane was added dropwise over 10 min. The mixture was stirred at 0° C. for 3 h, washed with 2% aq. citric acid, saturated sodium bicarbonate and brine, dried ($MgSO_4$) and evaporated and the residue purified by chromatography (EtOAc) to give the title compound (8.60 g) as beige solid.

$R_f$ 0.29 (ether)
MS 430 ($M^+$).

Similarly prepared were:

EXAMPLE 6

Ethyl 4-(4-pyridyloxypiperidin-1-yl) sulfonylmethyltetrahydropyran-4-carboxylate From intermediate 24 (1.0 g) and intermediate 29 (1.6 g) as colourless solid (1.45 g).

$R_f$ 0.37 (6% MeOH/dichloromethane 1% $NH_4OH$)
MS 412 ($M^+$)

EXAMPLE 7

Ethyl 4-(4-(4-Cyanophenoxy)piperidin-1-yl) sulfonylmethyltetrahydropyran-4-carboxylate From intermediate 24 (1.0 g) and intermediate 30 (1.24 g) as beige solid (1.20 g).

$R_f$ 0.32 (ether)
MS 436 ($M^+$)

EXAMPLE 8

Ethyl 4-(N-(2-(4-Chlorophenoxy)ethyl)-N-methylsulfamoylmethyl) tetrahydropyran-4-carboxylate From intermediate 24 (685 mg) and N-(2-(4-chlorophenoxy)ethyl)-N-methylamine (500 mg) as a colourless oil (944 mg, 84%).

$R_f$ 0.50 (2:1 ethyl acetate/hexane).
$M^+$420.

EXAMPLE 9

Ethyl 4-(4-(4-Chlorophenoxy)piperidin-1-yl) sulfonylmethyltetrahydropyran-4-carboxylate From intermediate 24 (3.28 g) and intermediate 31 (3.01 g) as a brown solid (4.47 g, 83%).

$R_f$ 0.40 (ether)

EXAMPLE 10 tert-Butyl 2-(N-(2-(4-Chlorophenoxy)ethyl)-N-methylsulfamoylmethyl)-3-methylbutanoate N-2-(4-Chlorophenoxy)ethyl-N-methylamine (300 mg) was added to a solution of intermediate 15 (438 mg) and triethylamine (1.2 ml) in dichloromethane (50 ml) at 0° C. The solution was stirred for 2 h, then washed with aqueous citric acid (5%, 50 ml), saturated bicarbonate solution (50 ml) and brine, dried ($MgSO_4$) and evaporated to give the title compound (469 mg, 69%) as a colourless oil.

$R_f$ 0.43 (2:1 hexane/ethyl acetate).

MS 420 ($M^+$)

Similarly prepared were:

EXAMPLE 11 tert-Butyl 2-[N-Methyl-N-(2-(4-Chlorophenoxy)-2,2-dimethylethyl) sulfamoyl]methyl-3-methylbutanoate From intermediate 27 (366 mg) and intermediate 15 (464 mg) as a colourless oil (464 mg, 61%).

$R_f$ 0.66 (2:1 hexane/ethyl acetate).

MS 448 ($M^+$)

EXAMPLE 12 tert-Butyl 2-(4-(4-Cyanophenoxyimino)piperidine-1-sulfonylmethyl)-5-(3,4,4-trimethyl-2,5-dioxoimidazolidin-1-yl) pentanoate Triethylamine (0.30 ml) was added via syringe to an ice-cold solution of intermediate 14 (0.437 g) and intermediate 36 (0.350 g) in anhydrous dichloromethane (20 ml), and the mixture stirred under nitrogen for 3 days at RT. After evaporation of the mixture under reduced pressure, the residue was dissolved in diethyl ether (40 ml) and washed with 2.5% aqueous citric acid (2×10 ml), water (10 ml), saturated sodium bicarbonate (10 ml), water (10 ml), saturated brine (10 ml), dried ($MgSO_4$) and concentrated in vacuo to yield the title compound (0.434 g, 69%) as a white solid.

$R_f$ 0.34 (diethyl ether)

Similarly prepared were:

EXAMPLE 13 tert-Butyl 2-(4-(4-Cyanophenoxyimino)piperidin-1-ylsulfonylmethyl)-3-methylbutanoic Acid From intermediate 36 (0.193 g) and intermediate 15 (0.181 g), as a colourless gum (0.087 g, 34%).

$R_f$ 0.40 (2% diethyl ether/dichloromethane)

EXAMPLE 14 tert-Butyl 2-(4-(4-Chlorobenzyloxyimino)piperidin-1-ylsulfonylmethyl)-3-methylbutanoate From intermediate 37 (0.48 g) and intermediate 15 (0.39 g), as a straw colourled gum (0.60 g, 92%).

$R_f$ 0.40 (2% diethyl ether/dichloromethane)

MS 473 ($MH^+$)

EXAMPLE 15

2-((2-Phenoxyethylsulfamoyl)methyl)-5-(3,4,4-trimethyl-2,5-dioxoimidazolidin-1-yl) pentanoic Acid To a stirred solution of example 1 (555 mg) in dioxane (25 ml) in an ice-salt bath was added a solution of lithium hydroxide (149 mg) in water (10 ml). Stirring was continued for 5 h then the mixture was diluted with water (50 ml) and extracted with diethyl ether (2×25 ml). The aqueous mixture was acidified with citric acid to pH 4, and then extracted with ethyl acetate (5×30 ml). The combined ethyl acetate extracts were washed with water (2×20 ml), brine (20 ml) and dried ($MgSO_4$). Filtration and evaporation of solvents in vacuo yielded the title compound (443 mg, 82%) as a white foam.

$R_f$ 0.39 (3:1 ethyl acetate/hexane)

MS 455 ($M^+$)

Similarly prepared were:

EXAMPLE 16

2-((N-Methyl-N-(2-phenoxyethyl)sulfamoyl)methyl)-5-(3,4,4-trimethyl-2,5-dioxoimidazolidin-1-yl) pentanoic Acid From example 2 (850 mg) as a colourless oil (642 mg, 78%).

$R_f$ (2:1 ethyl acetate/hexane).

MS 470 $M^+$)

EXAMPLE 17

2-((N-Methyl-N-(2-(4-Chlorophenoxy)ethyl)sulfamoyl)methyl)-5-(3,4,4-trimethyl-2,5-dioxoimidazolidin-1-yl) pentanoic Acid From example 3 (947 mg) as a colourless oil (772 mg, 84%).

$R_f$ 0.26 (3:1 ethyl acetate/hexane)

MS 504 ($M^+$)

EXAMPLE 18

2-((N-Methyl-(benzofuran-2-yl)methylsulfamoyl)methyl-5-(3,4,4-trimethyl-2,5-dioxoimidazolidin-1-yl)pentanoic Acid To a stirred solution of example 4 (575 mg) in dichloromethane (18 ml) at 0° C. was added trifluoroacetic acid (2 ml). The mixture was stirred for 16 h, with the temperature rising to RT. The solvent was removed in vacuo and the residue azeotroped with toluene (2×50 ml) to yield the title compound (515 mg, 100%) as a colourless oil.

$R_f$ 0.17 (2:1 ethyl acetate/hexane).

MS 480 ($M^+$)

EXAMPLE 19

4-(4-(4-Chlorophenyl)piperazin-1-yl)sulfonylmethyl)tetrahydropyran-4-carboxylic Acid Lithium hydroxide (6 g) was added to a solution of example 5 (8.6 g) in methanol (150 ml) and water (100 ml) and the solution was heated under reflux for 4 h. The mixture was cooled to RT, evaporated to half volume under reduced pressure and then the solution was washed with ether. The aqueous phase was acidified with citric acid to pH 5 and extracted with dichloromethane (4×100 ml). The solvent was washed with brine, dried ($MgSO_4$) and evaporated to give the title compound (5.60 g, 70%) as beige solid.

$R_f$ 0.20 (EtOAc)

MS 402 ($M^+$)

Similarly prepared were:

EXAMPLE 20

4-(4-Pyridyloxypiperidin-1-yl)sulfonylmethyl)
tetrahydropyran-4-carboxylic acid

From example 6 (1.45 g) as beige solid (0.20 g).
$R_f$ 0.20 (10% MeOH/dichloromethane 1% AcOH)
MS 384 ($M^+$)

EXAMPLE 21

4-(4-(4-Cyanophenoxy)piperidin-1-yl)
sulfonylmethyl-tetrahydropyran-4-carboxylic acid From example 7 (1.20 g) as colourless solid (0.25 g).
$R_f$ 0.54 (EtOAc+1% AcOH)
MS 408 ($M^+$)

EXAMPLE 22

4-(N-(2-(4-Chlorophenoxy)ethyl)-N-
methylsulfamoylmethyl)tetrahydropyran-4-
carboxylic Acid From example 8 (930 mg) as colourless solid (688 mg, 79%).
$R_f$ 0.30 (2:1 ethyl acetate/hexane).
MS 392 ($M^+$)

EXAMPLE 23

4-(4-(4-Chlorophenoxy)piperidin-1-yl)
sulfonylmethyl-tetrahydropyran-4-carboxylic Acid From example 9 (3.1 g) as colourless solid (2.6 g, 90%).
$R_f$ 0.40 (ether)
MS 416 (M−1)

EXAMPLE 24

2(N-(2-(4-Chlorophenoxy)ethyl)-N-
methylsulfamoyl-methyl)-3-methylbutanoic Acid

A solution of example 10 (465 mg) was dissolved in 30% trifluoruacetic acid in dichloromethane (50 ml) and the solution was stirred for 2 h. The solution was then evaporated under reduced pressure and the residue azeotroped to dryness with dichloromethane/hexanes (3×100 ml). The residue was dissolved in saturated sodium bicarbonate (50 ml) and washed with ether. The aqueous layer was acidified with citric acid and extracted with EtOAc (2×100 ml), the solvent dried (MgSO$_4$) and evaporated to give the title compound (403 mg, 100%) as a colourless oil.
$R_f$ 0.55 (2:1 ethyl acetate/hexane).
MS 363 ($M^+$)
Similarly prepared were:

EXAMPLE 25

2(N-Methyl-N-(2-(4-chlorophenoxy)-2,2-
dimethylethyl)sulfamoylmethyl)-3-methylbutanoic
Acid From example 11 (450 mg) as a colourless oil (379 mg, 97%).
$R_f$ 0.68 (2:1 ethyl acetate/hexane).
MS 392 ($M^+$)

EXAMPLE 26

2-(4-(4-Cyanophenoxyimino)piperidin-1-
ylsulfonylmethyl)-5-(3,4,4-trimethyl-2,5-dioxo-
imidazolidin-1-yl)pentanoic Acid Trifluoroacetic acid (2 ml) was added to a solution of example 12 ()0.434 g) in dichloromethane (18 ml), and the mixture stirred at room temperature. After 18 h, the reaction mixture was evaporated under reduced pressure, and the residue azeotroped twice with toluene. The resultant oil was purified by silica gel column chromatography, eluting with 4% methanol/dichloromethane, to provide the title compound (0.232 g, 59%) as a pale yellow gum.
$R_f$ 0.22 (4% methanol/dichloromethane)
MS 534 ($MH^+$)
Similarly prepared were:

EXAMPLE 27

2-(4-(4-Cyanophenoxyimino)piperidin-1-
ylsulfonylmethyl)-3-methylbutanoic Acid

From example 13 (0.087 g), as a colourless solid (0.085 g, 100%).
$R_f$ 0.49 (3% methanol/dichloromethane)
MS 394 ($MH^+$)

EXAMPLE 28

2-(4-(4-Chlorobenzyloxyimino)piperidin-1-
ylsulfonylmethyl)-3-methylbutanoic Acid From example 14 (0.60 g), as a white solid (0.42 g, 80%).
$R_f$ 0.50 (5% methanol/dichloromethane)
MS 417 ($MH^+$)

EXAMPLE 29

2-((2-Phenoxyethylsulfamoyl)methyl-5-(3,4,4-tri-
methyl-2,5-dioxoimidazolidin-1-yl)pentanoic Acid
N-Hydroxy Amide To a stirred solution of example 15 (440 mg) in dichloromethane (20 ml) at 0° C. was added EDC (189 mg) and O-tert-butyldimethylsilylhydroxylamine (141 mg). Stirring was continued for 5 h, with the temperature rising to RT, and then the mixture was diluted with dichloromethane (50 ml). The mixture was washed with water (3×20 ml), brine (20 ml) and dried (MgSO$_4$). Filtration and evaporation of solvents under reduced pressure gave a colourless oil that was dissolved in dichloromethane (15 ml) and treated with a solution of hydrogen chloride in diethyl ether (1M; 3.0 ml). The mixture was stirred for 1 h before the solvents were removed in vacuo and the residue was purified by silica gel column chromatography eluting with 3:12 ethyl acetate/hexane to yield the title compound (264 mg, 57%) as a white solid.
$R_f$ 0.32 (3:1 ethyl acetate/hexane).
MS 471 ($M^+$)
Similarly prepared were:

EXAMPLE 30

2-((N-Methyl-(2-phenoxyethyl)sulfamoyl)methyl)-5-
(3,4,4-trimethyl-2,5-dioxoimidazolidin-1-yl)
pentanoic Acid N-Hydroxy Amide From example 16 (500 mg) as a white solid (175 mg, 34%).
$R_f$ 0.16 (ethyl acetate).
MS 485 ($M^+$)

EXAMPLE 31

2-((N-Methyl-(2-(4-Chlorophenoxy)ethyl)
sulfamoyl)-methyl)-5-(3,4,4-trimethyl-2,5-
dioxoimidazolidin-1-yl)pentanoic Acid N-Hydroxy
Amide From example 17 (750 mg) as a white solid (332 mg, 43%).

$R_f$ 0.18 (ethyl acetate).
MS 519 (M$^+$)

EXAMPLE 32

2-((N-Methyl-(benzofuran-2-yl)methyl-sulfamoyl)
methyl)-5-(3,4,4-trimethyl-2,5-dioxoimidazolidin-1-
yl)pentanoic Acid N-Hydroxy Amide From example 18 (250 mg) as a white solid (98 mg, 38%).
$R_f$ 0.10 (9:1 ethyl acetate/methanol)
MS 495 (M$^+$).

EXAMPLE 33

2-(N-Methyl-N-(2-(4-chlorophenoxy)ethyl)-
sulfamoylmethyl)-3-methylbutanoic Acid N-
Hydroxy Amide From example 24 (400 mg) as a white foam (386 mg, 96%).
$R_f$ 0.46 (3:1 ethyl acetate/hexane)
M$^+$ 379.

EXAMPLE 34

2-(N-Methyl-N-(2-(4-chlorophenoxy)-2,2-
dimethylethyl)sulfamoylmethyl)-3-methylbutanoic
Acid N-Hydroxy Amide From example 25 (370 mg) as a white solid (141 mg, 37%).
$R_f$ 0.32 (3:1 ethyl acetate/hexane).
M$^+$ 407

EXAMPLE 35

4-(4-(4-Chlorophenyl)piperazin-1-yl)
sulfonylmethyl)tetrahydropyran-4-carboxylic Acid
N-Hydroxy Amide Hydrochloride Oxalyl chloride (4 ml) was added to a suspension of example 19 (5.6 g) in dichloromethane (100 ml) at 0° C., followed by dimethylformamide (1 drop). The mixture was stirred for 1 h, then evaporated in vacuo and the residue azeotroped with dichloromethane/hexanes (3×100 ml). The crude produce was dissolved in dichloromethane (50 ml) and triethylamine (5.80 ml) and O-TBDMS hyroxylamine (2.24 g) were added. The mixture was stirred for 3 h, then washed with water, aqueous sodium bicarbonate and brine, dried and evaporated. The crude product was dissolved in dry dichloromethane (100 ml) and HCl in ether (1M, 50 ml) was added dropwise. The mixture was vigorously stirred for 30 min, then the product collected by filtration and washed with ether (2×100 ml) to give the title compound (5.0 g) as colourless powder.

$R_f$ 0.53 (10% MeOH/dichloromethane 1% NH$_4$OH)
MS 418 (M$^+$)
Similarly prepared were:

EXAMPLE 36

4-(4-(4-Pyridyloxy)piperidin-1-yl)sulfonylmethyl)-
tetrahydropyran-4-carboxylic Acid N-Hydroxy
Amide Hydrochloride From example 20 (0.19 g) as white solid (0.12 g).
$R_f$ 0.25 (7% MeOH/dichloromethane 1% NH$_4$OH)
MS 400 M$^+$).

EXAMPLE 37

4-(4-(4-Cyanophenoxy)piperidin-1-yl)
sulfonylmethyl)-tetrahydro-pyran-4-carboxylic Acid
N-Hydroxy Amide From example 21 (0.25 g) as white solid (5.5 mg.)
$R_f$ 0.32 (5% MeOH/dichloromethane)
MS 423 M$^+$).

EXAMPLE 38

4(N-(2-(4-Chlorophenoxy)ethyl)-N-
methylsulfamoylmethyl)tetrahydropyran-4-
carboxylic Acid N-Hydroxy Amide From example 22 (650 mg) as a colourless solid (412 mg, 74%).
$R_f$ 0.24 (ethyl acetate).
M$^+$ 407.

EXAMPLE 39

4-(4-(4-Chlorophenoxy)piperidin-1-yl)
sulfonylmethyltetrahydroyran-4-carboxylic Acid N-
Hydroxy Amide From example 23 (2.69 g) as colourless solid (2.40 g, 86%).
$R_f$ 0.22 (5% MeOH/dichloromethane)
MS 431 (M−1)

EXAMPLE 40

2-[4-(4-Cyanophenoxyimino)piperidin-1-
ylsulfonylmethyl]-5-(3,4,4-trimethyl-2,5-
dioxoimidazolidin-1-yl)pentanoic Acid N-Hydroxy
Amide EDC (0.102 g) was added to a suspension of O-tert-butyldimethylsilylhydroxylamine (0.066 g) and example 26 (0.218 g) in dichloromethane (20 ml), and the mixture stirred at room temperature for 18 h. The solvent was then evaporated under reduced pressure. The residue was dissolved in ethyl acetate (50 ml) and washed with water (2×10 ml), saturated sodium bicarbonate (20 ml), water (10 ml), saturated brine (10 ml) and dried (MgSO$_4$). The organic phase was then evaporated in vacuo, the residue dissolved in tetrahydrofuran (5 ml), cooled in an ice-bath, and treated with tetrabutylammonium fluoride (1.0 M solution in tetrahydrofuran; 0.45 ml). After 10 min, the reaction was quenched with acetic acid (0.5 ml) and partitioned between water (30 ml) and hexane (20 ml). The hexane was decanted and the aqueous phase reshaken with hexane (20 ml). The aqueous phase was then extracted with ethyl acetate (2×20 ml), and the combined organic extracts were washed with a 1:1:1 mixture of water, saturated sodium bicarbonate and saturated brine (15 ml). The organic layer was further washed with saturated brine (15 ml), then dried (MgSO$_4$) and evaporated under reduced pressure to yield the title compound (0.185 g, 82%) as a white solid.

$R_f$ 0.16 (5% methanol/dichloromethane)
MS 549 (MH$^+$)
Similarly prepared were:

EXAMPLE 41

2-(4-(4-Cyanophenoxyimino)piperidin-1-
ylsulfonylmethyl)-3-methylbutanoic Acid N-
Hydroxy Amide From example 27 (0.085 g), as a white solid (0.017 g, 22%).
$R_f$ 0.13 (3% methanol/dichloromethane)
MS 409 (MH$^+$).

EXAMPLE 42

2-(4-(4-Chlorobenzyloxyimino)piperidin-1-
ylsulfonylmethyl)-3-methylbutanoic Acid N-
Hydroxy Amide ECD (0.251 g) was added to a solution of O-tert-butyldimethylsilylhydroxylamine (0.148 g) and example 28

(0.42 g) in dichloromethane (40 ml), and the mixture stirred at room temperature for 4 h. The solvent was then evaporated under reduced pressure, and the residue was dissolved in ethyl acetate (60 ml) and washed with 1% citric acid (20 ml), water (20 ml), saturated sodium bicarbonate (20 ml), water (10 ml), saturated brine (15 ml) and dried ($MgSO_4$). The organic phase was then evaporated in vacuo, and the residue purified by silica gel column chromatography with 4% methanol/dichloromethane, pre-eluting the column with 4% methanol/5% triethylamine/dichloromethane, to give a white solid (0.41 g). The white solid was then dissolved in dichloromethane (20 ml) and treated with hydrogen chloride, as a 1.0 M solution in diethyl ether (3.0 ml). After 20 min. at room temperature, the solvents were removed and the residue triturated with a mixture of dichloromethane and diethyl ether to provide the title compound (0.294 g, 67%) as a colourless solid.

$R_f$ 0.14 (5% methanol/dichloromethane)
MS 432 ($MH^+$)
HPLC-MS Conditions

In the following experimental descriptions, HPLC-MS was performed on a Hewlett Packard 1100 LC using a Phenomenex Luna C18, 50×2.1 mm column at 35° C., running a solvent A: solvent B gradient of 95:5 to 35:65 in 4.70 min and to 0:100 in 1.50 min at a flow rate of 0.90 mL/min. Solvent A and solvent B are 95% water:5% acetonitrile 0.1% formic acid and 5% water:95% acetonitrile 0.1% formic acid respectively. MS spectra were acquired at 1 cone voltage (30V), on a Micromass Quattro (triple quadrupole) instrument.

EXAMPLE 43

2-((N-Ethyl-N-(2-methoxyethyl)-sulfamoylmethyl)-5-(3,4,4-trimethyl-2,5-dioxoimidazolidin-1-yl)-pentanoic Acid N-Hydroxy Amide (2-Methoxyethyl)ethylamine (0.1 mmol) was added to a solution of intermediate 15 (0.1 mmol) and N-methylmorpholine (1.1 eq) in dichloromethane (1 ml) at 0° C. in a scintillation vials and the solutions was stirred overnight at room temperature. The solutions was washed with 0.2 M HCl (1 ml) and saturated bicarbonate solution, then evaporated to dryness. The crude product was dissolved in 50% trifluoroacetic acid/dichloromethane (1 ml) and stirred overnight at room temperature, then evaporated to dryness and azeotroped with toluene. The crude acids were then taken up in dichloromethane, and then treated with one equivalent each of ECD, hydroxylamine hydrochloride and N-methylmorpholine for 18 h. The solution was then washed with water and aqueous sodium bicarbonate, and evaporated. The crude produce was purified by preparative HPLC, to give the title compound as a colourless foam (10.8 mg)

HPLC $R_t$ 5.32 min.
MS 436 ($M^+$)

EXAMPLE 44

2-(3,3-Diphenylpropylsulfamoylmethyl)-5-(3,4,4-trimethyl-2,5-dioxo-imidazolidin-1-yl)-pentanoic Acid N-Hydroxy Amide From intermediate 15 and 3,3-diphenylpropylamine, as a white solid (14.3 mg).
HPLC $R_t$ 6.70 min.
MS 544 ($M^+$)

EXAMPLE 45

2-(Cyclohexylmethylsulfamoylmethyl)-5-(3,4,4-trimethyl-2,5-dioxoimidazolidin-1-yl)-pentanoic Acid N-Hydroxy Amide From intermediate 15 and cyclohexylmethylamine, as a beige solid (5.5 mg).
HPLC $R_t$ 5.58 min.
MS 446 ($M^+$)

EXAMPLE 46

2-(1-Methyl-3-phenylpropylsulfamoylmethyl)-5-(3,4,4-trimethyl-2,5-dioxoimidazolidin-1-yl)pentanoic Acid N-hydroxy Amide From intermediate 15 and 1-methyl-3-phenylpropylamine, as a white solid (24.7 mg).
HPLC $R_t$ 5.88 min.
MS 482 ($M^+$)

EXAMPLE 47

2-((3-Phenylpropyl)sulfamoylmethyl)-5-(3,4,4-trimethyl-2,5-dioxo-imidazolidin-1-yl)-pentanoic Acid N-Hydroxy Amide HPLC $R_t$ 5.61 min.
MS 468 ($M^+$)

EXAMPLE 48

2-((N-Methyl-N-octylsulfamoyl)methyl)-5-(3,4,4-trimethyl-2,5-dioxoimidazolidin-1-yl)-pentanoic Acid N-Hydroxy Amide From intermediate 15 and octylmethylamine, as a colourless solid (19.1 mg)
HPLC $R_t$ 7.42 min.
MS 476 ($M^+$)

EXAMPLE 49

2-(N-(2-Cyanoethyl)-N-octylsulfamoylmethyl)-5-(3,4,4-trimethyl-2,5-dioxoimidazolidin-1-yl)-pentanoic Acid N-Hydroxy Amide From intermediate 15 and (2-cyanoethyl)octylamine, as a beige solid (3.1 mg).
HPLC $R_t$ 7.23 min.
MS 515 ($M^+$)

EXAMPLE 50

2-(N-(2-(4-Chlorophenoxy)-1-methylethyl)-N-methylsulfamoylmethyl)-5-(3,4,4-trimethyl-2,5-dioxoimidazolidin-1-yl)-pentanoic Acid N-Hydroxy Amide From intermediate 15 and N-(2-(4-Chlorophenoxy)-1-methylethyl))methylamine, as a beige solid (7.3 mg).
HPLC $R_t$ 6.46 min.
MS 532 ($M^+$)

EXAMPLE 51

2-(N-methyl-N-phenethylsulfamoylmethyl)-5-(3,4,4-trimethyl-2,5-dioxoimidazolidin-1-yl)-pentanoic Acid N-Hydroxy Amide From intermediate 15 and N-(phenethyl)methyamine, as a white solid (13.2 mg).
HPLC $R_t$ 5.22 min.
MS 468 ($M^+$)

EXAMPLE 52

2-(N-(2-(2-Chlorophenoxy)ethyl)-N-methyl-sulfamoylmethyl)-5-(3,4,4-trimethyl-2,5-dioxoimidazolidin-1-yl)-pentanoic Acid N-Hydroxy Amide From intermediate 15 and N-(2-(2-chlorophenoxy)ethyl)methylamine, as a brown solid (5.5 mg).

HPLC R$_t$ 5.68 min.
MS 518 (M$^+$)

EXAMPLE 53

2-(N-Ethyl-N-phenylsulfamoylmethyl)-5-(3,4,4-trimethyl-2,5-dioxo-imidazolidin-1-yl)-pentanoic Acid N-Hydroxy Amide From intermediate 15 and N-ethylaniline, and a colourless solid (9.0 mg).
HPLC R$_t$ 5.89 min.
MS 454 (M$^+$)

EXAMPLE 54

2-(N-(4-Chlorophenyl)-N-methylsulfamoylmethyl)-5-(3,4,4-trimethyl-2,5-dioxoimidazolidin-1-yl) pentanoic Acid N-Hydroxy Amide From intermediate 15 and N-(4-chlorophenyl) methylamine, as a white solid (3.2 mg).
HPLC R$_t$ 5.69 min.
MS 474 (M$^+$)

What is claimed is:
1. A compound represented by formula (I):

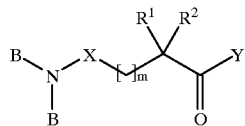

wherein
m is 0–2;
X is S(O)$_{1-2}$;
Y is NHOH;
R$^1$ is H or a group (substituted or unsubstituted with R$^7$) selected from the group consisting of C$_{1-6}$ alkyl, C$_{2-6}$ alkenyl, aryl, C$_{1-6}$ alkyl-aryl, heteroaryl, C$_{1-6}$ alkyl-heteroaryl, heterocycloalkyl, C$_{1-6}$ alkyl-heterocycloalkyl, cycloalkyl, and C$_{1-6}$ alkyl-cycloalkyl, and R$^2$ is H or C$_{1-6}$ alkyl;
or CR$^1$R$^2$ is a cycloalkyl or heterocycloalkyl ring substituted or unsubstituted with R$^7$ or a group (substituted or unsubstituted with R$^7$) selected from the group consisting of C$_{1-6}$ alkyl, aryl, C$_{1-6}$ alkyl-aryl, heteroaryl, and C$_{1-6}$ alkyl-heteroaryl;
each B is the same or different and is selected from the group consisting of H, C$_{1-6}$ alkyl-aryl, C$_{1-6}$ alkyl, cycloalkyl, C$_{1-6}$ alkyl-cycloalkyl, cycloalkenyl, heterocycloalkenyl, C$_{1-6}$ alkyl-heteroaryl, heterocycloalkyl, C$_{1-6}$ alkyl-heterocycloalkyl, aryl, and heteroaryl, any of which groups is substituted or unsubstituted by a substituent selected from the group consisting of R$^3$, C$_{1-6}$ alkyl-R$^3$, C$_{2-6}$ alkenyl-R$^3$, aryl (substituted or unsubstituted with R$^3$), aryl-C$_{1-6}$ alkyl-R$^3$, C$_{1-6}$ alkyl-aryl (substituted or unsubstituted with R$^3$), C$_{1-6}$ alkyl-heteroaryl (substituted or unsubstituted with R$^3$), aryl-C$_{2-6}$ alkenyl-R$^5$, heteroaryl (substituted or unsubstituted with R$^3$), heteroaryl-C$_{1-6}$ alkyl-R$^3$, cycloalkyl (substituted or unsubstituted with R$^3$), and heterocycloalkyl (substituted or unsubstituted with R$^3$), provided that NB$_2$ is not NH$_2$,
or B—N—B is a heterocycloalkyl ring substituted with =O or =NOR$^4$,
or, when neither R$^1$ nor R$^2$ is H, B—N—B is a heterocycloalkyl or heterocyclalkenyl ring substituted or unsubstituted by a substituent selected from the group consisting of R$^3$, C$_{1-6}$ alkyl-R$^3$, C$_{2-6}$ alkenyl-R$^3$, aryl (substituted or unsubstituted with R$^3$), aryl-C$_{1-6}$ alkyl-R$^3$, C$_{1-6}$ alkyl-aryl (substituted or unsubstituted with R$^3$), C$_{1-6}$ alkyl-heteroaryl (substituted or unsubstituted with R$^3$), aryl-C$_{2-6}$ alkenyl-R$^5$, heteroaryl (substituted or unsubstituted with R$^3$), heteroaryl-C$_{1-6}$ alkyl-R$^3$, cycloalkyl (substituted or unsubstituted with R$^3$), and heterocycloalkyl (substituted or unsubstituted with R$^3$);
R$^3$ is selected from the group consisting of C$_{1-6}$ alkyl, C$_{2-6}$ alkenyl-R$^5$, halogen, CN, NO$_2$, N(R$^4$)$_2$, OR$^4$, C(=NOR$^6$)R$^4$, CON(R$^4$)$_2$, COR$^4$, CO$_2$R$^8$, NR$^4$R$^5$, S(O)$_{0-2}$R$^6$, and SO$_2$N(R$^4$)$_2$;
R$^4$ is selected from the group consisting of H, C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl, and C$_{1-6}$ alkyl-heterocycloalkyl, wherein said group is substituted or unsubstituted with a substituent selected from the group consisting of R$^6$, COR$^6$, SO$_{0-2}$R$^6$, CO$_2$R$^6$, OR$^6$, CONR$^8$R$^6$, NR$^8$R$^6$, halogen, CN, SO$_2$NR$^8$R$^6$, and NO$_2$, and for each case of N(R$^4$)$_2$ the R$^4$ groups are the same or different or N(R$^4$)$_2$ is heterocycloalkyl substituted or unsubstituted with a substituent selected from the group consisting of R$^6$, COR$^6$, SO$_{2-2}$R$^6$, CO$_2$R$^6$, OR$^6$, CONR$^8$R$^6$, NR$^8$R$^6$, halogen, CN, SO$_2$NR$^8$R$^6$, and NO$_2$;
R$^5$ is selected from the group consisting of COR$^4$, CON(R$^4$)$_2$, CO$_2$R$^6$, and SO$_2$R$^6$;
R$^6$ is selected from the group consisting of C$_{1-6}$ alkyl, aryl, C$_{1-6}$ alkyl-aryl, heteroaryl, and C$_{1-6}$ alkyl-heteroaryl;
R$^7$ is selected from the group consisting of OR$^4$, COR$^4$, CO$_2$R$^8$, CON(R$^4$)$_2$, NR$^4$R$^5$, S(O)$_{0-2}$ R$^6$, SO$_2$N(R$^4$)$_2$, halogen, CN, and cycloimidyl (substituted or unsubstituted with R$^8$); and
R$^8$ is H or C$_{1-6}$ alkyl;
or the salts, solvates, hydrates, N-oxides, protected amino, protected carboxy, or protected hydroxamic acid derivatives thereof; and
wherein provided that, when R$^7$ is CON(R$^4$)$_2$, R$^4$ is not substituted with CONR$^6$R$^8$.
2. The compound, according to claim 1, wherein X is SO$_2$.
3. The compound, according to claim 1, wherein R$^3$ is selected from the group consisting of C$_{1-6}$ alkyl, C$_{2-6}$ alkenyl-R$^5$, halogen, CN, NO$_2$, N(R$^4$)$_2$, OR$^4$, COR$^4$, NR$^4$R$^5$, S(O)$_{0-2}$R$^6$, and SO$_2$N(R$^4$)$_2$.
4. The compound, according to claim 1, wherein R$^7$ is selected from the group consisting of CON(R$^4$)$_2$, NR$^4$R$^5$, SO$_2$N(R$^4$)$_2$, and cycloimidyl.
5. The compound, according to claim 1, wherein R$^1$ is selected from the group consisting of substituted or unsubstituted C$_{1-6}$ alkyl, C$_{1-6}$ alkyl-heteroaryl, and C$_{1-6}$ alkyl-heterocycloalkyl.
6. The compound, according to claim 1, wherein CR$^1$R$^2$ is substituted or unsubstituted cycloalkyl or heterocycloalkyl.
7. The compound, according to claim 1, wherein independently each B is selected from the group consisting of substituted or unsubstituted alkyl, cycloalkyl, heterocycloalkyl, C$_{1-6}$ alkyl-aryl, and C$_{14}$ alkyl-heteroaryl.
8. The compound, according to claim 1, wherein B—N—B is substituted or unsubstituted heterocycloalkyl substituted or unsubstituted with =NOR$^4$.
9. The compound, according to claim 1, selected from the group consisting of methyl 2-((2-phenoxyethylsulfamoyl)methyl)-5-(3,4,4-trimethyl-2,5-dioxoimidazolidin-1-yl)pentanoate,
methyl 2-((N-methyl-(2-phenoxyethyl)sulfamoyl)methyl)-5-(3,4,4-trimethyl-2,5-dioxoimidazolidin-1-yl)pentanoate,
methyl 2-((N-methyl-(2-(4-chlorophenoxy)ethyl)sulfamoyl)methyl)-5-(3,4,4-trimethyl-2,5-dioxoimidazolidin-1-yl)pentanoate,
tert-butyl 2-((N-methyl-(benzofuran-2-yl)methylsulfamoyl)methyl)-5-(3,4,4-trimethyl-2,5-dioxoimidazolidin-1-yl)pentanoate,
2-((2-phenoxyethylsulfamoyl)methyl)-5-(3,4,4-trimethyl-2,5-dioxoimidazolidin-1-yl)pentanoic acid,
2-((N-methyl-N-(2-(4-chlorophenoxy)ethyl)sulfamoyl)methyl)-5-(3,4,4-trimethyl-2,5-dioxoimidazolidin-1-yl)pentanoic acid,
2-((N-methyl-(benzofuran-2-yl)methylsulfamoyl)methyl)-5-(3,4,4-trimethyl-2,5-dioxoimidazolidin-1-yl)pentanoic acid,
2-((2-phenoxyethylsulfamoyl)methyl)-5-(3,4,4-trimethyl-2,5-dioxoimidazolidin-1-yl)pentanoic acid N-hydroxy amide,
2-((N-methyl-(2-phenoxyethyl)sulfamoyl)methyl)-5-(3,4,4-trimethyl-2,5-dioxoimidazolidin-1-yl)pentanoic acid N-hydroxy amide,
2-((N-methyl-(2-(4-chlorophenoxy)ethyl)sulfamoyl)methyl)-5-(3,4,4-trimethyl-2,5-dioxoimidazolidin-1-yl)pentanoic acid N-hydroxy amide, and
2-((N-methyl-(benzofuran-2-yl)methyl-sulfamoyl)methyl)-5-(3,4,4-trimethyl-2,5-dioxoimidazolidin-1-yl)pentanoic acid N-hydroxy amide.

10. The compound, according to claim 1, wherein said compound is selected from the group consisting of:
ethyl 4-(4-(4-Chlorophenyl)piperazin-1-yl)sulfonylmethyl)-tetrahydropyran-4-carboxylate,
ethyl 4-(4-pyridyloxypiperidin-1-yl)sulfonylmethyl-tetrahydropyran-4-carboxylate,
ethyl 4-(4-(4-Cyanophenoxy)piperidin-1-yl)sulfonylmethyl-tetrahydropyran-4-carboxylate,
ethyl 4-(N-(2-(4-Chlorophenoxy)ethyl)-N-methylsulfamoyl-methyl)tetrahydropyran-4-carboxylate,
ethyl 4-(4-(4-Chlorophenoxy)piperidin-1-yl)sulfonylmethyl-tetrahydropyran-4-carboxylate,
tert-Butyl 2-(N-(2-(4-Chlorophenoxy)ethyl)-N-methyl-sulfamoylmethyl)-3-methylbutanoate,
tert-Butyl 2-[N-Methyl-N-(2-(4-Chlorophenoxy)-2,2-dimethylethyl)sulfamoyl]methyl-3-methylbutanoate,
tert-Butyl 2-(4-(4-Cyanophenoxyimino)piperidine-1-sulfonylmethyl)-5-(3,4,4-trimethyl-2,5-dioxoimidazolidin-1-yl)pentanoate,
tert-Butyl 2-(4-(4-Cyanophenoxyimino)piperidin-1-ylsulfonylmethyl)-3-methylbutanoic Acid,
tert-Butyl 2-(4-(4-Chlorobenzyloxyimino)piperidin-1-ylsulfonylmethyl)-3-methylbutanoate,
2-((N-Methyl-N-(2-phenoxyethyl)sulfamoyl)methyl)-5-(3,4,4-trimethyl-2,5-dioxoimidazolidin-1-yl)pentanoic acid,
4-(4-(4-Chlorophenyl)piperazin-1-yl)sulfonylmethyl)-tetrahydropyran-4-carboxylic acid,
4-(4-Pyridyloxypiperidin-1-yl)sulfonylmethyl)-tetrahydropyran-4-carboxylic acid,
4-(4-(4-Cyanophenoxy)piperidin-1-yl)sulfonylmethyl-tetrahydropyran-4-carboxylic acid,
4-(N-(2-(4-Chlorophenoxy)ethyl)-N-methylsulfamoylmethyl)tetrahydropyran-4-carboxylic acid,
4-(4-(4-Chlorophenoxy)piperidin-1-yl)sulfonylmethyl-tetrahydropyran-4-carboxylic Acid,
2-(N-(2-(4-Chlorophenoxy)ethyl)-N-methylsulfamoyl-methyl)-3-methylbutanoic Acid,
2-(N-Methyl-N-(2-(4-chlorophenoxy)-2,2-dimethylethyl)-sulfamoylmethyl)-3-methylbutanoic Acid,
2-(4-(4-Cyanophenoxyimino)piperidin-1-ylsulfonylmethyl)-5-(3,4,4-trimethyl-2,5-dioxoimidazolidin-1-yl)pentanoic Acid,
2-(4-(4-Cyanophenoxyimino)piperidin-1-ylsulfonylmethyl)-3-methylbutanoic Acid,
2-(4-(4-Chlorobenzyloxyimino)piperidin-1-ylsulfonylmethyl)-3-methylbutanoic Acid,
2-(N-Methyl-N-(2-(4-chlorophenoxy)ethyl)-sulfamoylmethyl)-3-methylbutanoic Acid N-Hydroxy Amide,
2-(N-Methyl-N-(2-(4-chlorophenoxy)-2,2-dimethyl-ethyl)sulfamoylmethyl)-3-methylbutanoic Acid N-Hydroxy Amide,
4-(4-(4-Pyridyloxy)piperidin-1-yl)sulfonylmethyl)-tetrahydropyran-4-carboxylic Acid N-Hydroxy Amide Hydrochloride,
4-(4-(4-Cyanophenoxy)piperidin-1-yl)sulfonylmethyl-tetrahydropyran-4-carboxylic Acid N-Hydroxy Amide,
4-(N-(2-(4-Chlorophenoxy)ethyl)-N-methylsulfamoyl-methyl)tetrahydropyran-4-carboxylic Acid N-Hydroxy Amide,
4-(4-(4-Chlorophenoxy)piperidin-1-yl)sulfonylmethyl-tetrahydropyran-4-carboxylic Acid N-Hydroxy Amide,
2-[4-(4-Cyanophenoxyimino)piperidin-1-ylsulfonylmethyl]-5-(3,4,4-trimethyl-2,5-dioxoimidazolidin-1-yl)pentanoic Acid N-Hydroxy Amide,
2-(4-(4-Cyanophenoxyimino)piperidin-1-ylsulfonylmethyl)-3-methylbutanoic Acid N-Hydroxy Amide,
2-(4-(4-Chlorobenzyloxyimino)piperidin1-ylsulfonylmethyl)-3-methylbutanoic Acid N-Hydroxy Amide,
2-((N-Ethyl-N-(2-methoxyethyl)-sulfamoylmethyl)-5-(3,4,4-trimethyl-2,5-dioxoimidazolidin-1-yl)-pentanoic Acid N-Hydroxy Amide,
2-(3,3-Diphenylpropylsulfamoylmethyl)-5-(3,4,4-trimethyl-2,5-dioxo-imidazolidin-1-yl)-pentanoic Acid N-Hydroxy Amide,
2-(Cyclohexylmethylsulfamoylmethyl)-5-(3,4,4-trimethyl-2,5-dioxoimidazolidin-1-yl)-pentanoic Acid N-Hydroxy Amide,
2-(1-Methyl-3-phenylpropylsulfamoylmethyl)-5-(3,4,4-trimethyl-2,5-dioxoimidazolidin-1-yl)pentanoic Acid N-hydroxy Amide,
2-((3-Phenylpropyl)sulfamoylmethyl)-5-(3,4,4-trimethyl-2,5-dioxo-imidazolidin-1-yl)-pentanoic Acid N-Hydroxy Amide,
2-((N-Methyl-N-octylsulfamoyl)methyl)-5-(3,4,4-trimethyl-2,5-dioxoimidazolidin-1yl)-pentanoic Acid N-Hydroxy Amide,
2-(N-(2-Cyanoethyl)-N-octylsulfamoylmethyl)-5-(3,4,4-trimethyl-2,5-dioxoimidazolidin-1-yl)-pentanoic Acid N-Hydroxy Amide, 2-(N-(2-(4-Chlorophenoxy)-1-methylethyl)-N-methylsulfamoylmethyl)-5-(3,4,4-trimethyl-2,5-dioxo-imidazolidin-1-yl)-pentanoic Acid N-Hydroxy Amide, 2-(N-methyl-N-phenethylsulfamoylmethyl)-5-(3,4,4-trimethyl-2,5-dioxoimidazolidin-1-yl)-pentanoic Acid N-Hydroxy Amide, 2-(N-(2-(2-Chlorophenoxy)ethyl)-N-methyl-sulfamoylmethyl)-5-(3,4,4-trimethyl-2,5-dioxoimidazolidin-1-yl)-pentanoic Acid N-Hydroxy Amide, 2-(N-Ethyl-N-phenylsulfamoylmethyl)-5-(3,4,4-trimethyl-2,5-dioxo-imidazolidin-1-yl)-pentanoic Acid N-Hydroxy Amide, and 2-(N-(4-Chlorophenyl)-N-methylsulfamoylmethyl)-5-(3,4,4-trimethyl-2,5-dioxoimidazolidin-1yl)pentanoic Acid N-Hydroxy Amide.

11. The compound, according to claim 1, in the form of a single enantiomer or diastereomer.

12. A pharmaceutical composition comprising a compound of claim 1, and a pharmaceutically-acceptable diluent or carrier.

13. A method for the treatment of a condition associated with matrix metalloproteinases or that is mediated by TNF α or enzymes involved in the shedding of L-selectin, CD23, the TNF receptors, IL-6 receptors, or IL-1 receptors, wherein said method comprises administration of an effective amount of a composition comprising a compound represented by formula (I):

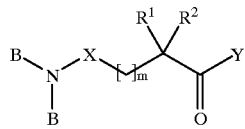

wherein
m is 0–2;
X is $S(O)_{1-2}$;
Y is OH or NHOH;
$R^1$ is H or a group (substituted or unsubstituted with $R^7$) selected from the group consisting of $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl, and $C_{1-6}$ alkyl-cycloalkyl, and $R^2$ is H or $C_{1-6}$ alkyl;
or $CR^1R^2$ is a cycloalkyl or heterocycloalkyl ring substituted or unsubstituted with $R^7$ or a group (substituted or unsubstituted with $R^7$) selected from the group consisting of $C_{1-6}$ alkyl, aryl, $C_{1-6}$ alkyl-aryl, heteroaryl, and $C_{1-6}$ alkyl-heteroaryl;
each B is the same or different and is selected from the group consisting of H, $C_{1-6}$ alkyl-aryl, $C_{1-6}$ alkyl, cycloalkyl, $C_{1-6}$ alkyl-cycloalkyl, cycloalkenyl, heterocycloalkenyl, $C_{1-6}$ alkylheteroaryl, heterocycloalkyl, $C_{1-6}$ alkyl-heterocycloalkyl, aryl, and heteroaryl, any of which groups is substituted or unsubstituted by a substituent selected from the group consisting of $R^3$, $C_{1-6}$ alkyl-$R^3$, $C_{2-6}$ alkenyl-$R^3$, aryl (substituted or unsubstituted with $R^3$), aryl-$C_{1-6}$ alkyl-$R^3$, $C_{1-6}$ alkyl-aryl (substituted or unsubstituted with $R^3$), $C_{1-6}$ alkyl-heteroaryl(substituted or unsubstituted with $R^3$), aryl-$C_{2-6}$ alkenyl-$R^5$, heteroaryl (substituted or unsubstituted with $R^3$), heteroaryl-$C_{1-6}$ alkyl-$R^3$, cycloalkyl (substituted or unsubstituted with $R^3$), and heterocycloalkyl (substituted or unsubstituted with $R^3$), provided that $NB_2$ is not $NH_2$, or B—N—B is a heterocycloalkyl ring substituted with =O or =$NOR^4$,
or, when neither $R^1$ nor $R^2$ is H, B—N—B is a heterocycloalkyl or heterocyclalkenyl ring substituted or unsubstituted by a substituent selected from the group consisting of $R^3$, $C_{1-6}$ alkyl-$R^3$, $C_{2-6}$ alkenyl-$R^3$, aryl (substituted or unsubstituted with $R^3$), aryl-$C_{1-6}$ alkyl-$R^3$, $C_{1-6}$ alkyl-aryl (substituted or unsubstituted with $R^3$), $C_{1-6}$ alkyl-heteroaryl (substituted or unsubstituted with $R^3$), aryl-$C_{2-6}$ alkenyl-$R^5$, heteroaryl (substituted or unsubstituted with $R^3$), heteroaryl-$C_{1-6}$ alkyl-$R^3$, cycloalkyl (substituted or unsubstituted with $R^3$), and heterocycloalkyl (substituted or unsubstituted with $R^3$);

$R^3$ is selected from the group consisting of $C_{1-6}$ alkyl, $C_{2-6}$ alkenyl-$R^5$, halogen, CN, $NO_2$, $N(R^4)_2$, $OR^4$, $C(=NOR^6)R^4$, $CON(R^4)_2$, $COR^4$, $CO_2R^8$, $NR^4R^5$, $S(O)_{0-2}R^6$, and $SO_2N(R^4)_2$;

$R^4$ is selected from the group consisting of H, $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl, and $C_{1-6}$ alkyl-heterocycloalkyl, wherein said group is substituted or unsubstituted with a substituent selected from the group consisting of $R^6$, $COR^6$, $SO_{0-2}R^6$, $CO_2R^6$, $OR^6$, $CONR^8R^6$, $NR^8R^6$, halogen, CN, $SO_2NR^8R^6$, and $NO_2$, and for each case of $N(R^4)_2$ the $R^4$ groups are the same or different or $N(R^4)_2$ is heterocycloalkyl substituted or unsubstituted with a substituent selected from the group consisting of $R^6$, $COR^6$, $SO_{0-2}$ $R^6CO_2R^6$, $OR^6$, $CONR^8R^6$, $NR^8R^6$, halogen, CN, $SO_2NR^8R^6$, and $NO_2$;

$R^5$ is selected from the group consisting of $COR^4$, CON$(R^4)_2$, $CO_2R^6$, and $SO_2R^6$;

$R^6$ is selected from the group consisting of $C_{1-6}$ alkyl, aryl, $C_{1-6}$ alkyl-aryl, heteroaryl, and $C_{1-6}$ alkyl-heteroaryl;

$R^7$ is selected from the group consisting of $OR^4$, $COR^4$, $CO_2R^8$, CON$(R^4)_2$, $NR^4R^5$, $S(O)_{0-2}$ $R^6$, $SO_2N(R^4)_2$, halogen, CN, and cycloimidyl (substituted or unsubstituted with $R^8$); and $R^8$ is H or $C_{1-6}$ alkyl;

and the salts, solvates, hydrates, N-oxides, protected amino, protected carboxy, or protected hydroxamic acid derivatives thereof.

14. The method, according to claim 13, wherein said condition is selected from the group consisting of cancer, inflammation and inflammatory diseases, tissue degeneration, periodontal disease, ophthalmological disease, dermatological disorders, fever, cardiovascular effects, haemorrhage, coagulation and acute phase response, cachexia, anorexia, acute infection, HIV infection, shock states, graft versus host reactions, autoimmune disease, reperfusion injury, meningitis, migraine and aspirin-independent anti-thrombosis.

15. The method, according to claim 13, wherein said condition is selected from the group consisting of tumour growth, angiogenesis, tumour invasion and spread, metastases, malignant ascites, and malignant pleural effusion.

16. The method, according to claim 13, wherein said condition is selected from the group consisting of cerebral ischaemia, ischaemic heart disease, rheumatoid arthritis, osteoarthritis, osteoporosis, asthma, multiple sclerosis, neurodegeneration, Alzheimer's, atherosclerosis, stroke, vasculitis, Crohn's disease and ulcerative colitis.

17. The method, according to claim 13, wherein said condition is selected from the group consisting of conical ulceration, retinopathy and surgical wound healing.

18. The method, according to claim 13, wherein said condition is selected from the group consisting of psoriasis, atopic dermatitis, chronic ulcers and epidermolysis bullosa.

19. The method, according to claim 13, wherein said condition is selected from the group consisting of periodontitis and gingivitis.

20. The method, according to claim 13, wherein said condition is selected from the group consisting of rhinitis, allergic conjunctivitis, eczema, and anaphylaxis.

21. The method, according to claim 13, wherein said condition is selected from the group consisting of restenosis, congestive heart failure, endometriosis, atherosclerosis, and endosclerosis.

22. The method, according to claim 13, wherein said condition is selected from the group consisting of pelvic inflammatory disease (PID), age-related macular degeneration, osteoporosis, and cancer-induced bone resorption.

23. The method, according to claim 13, wherein said condition is a lung disease.

24. The method, according to claim 23, wherein said condition is selected from the group consisting of cystic fibrosis adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulomatosis, pulmonary lymphangioleiomyomatosis, (LAM) and chronic obstructive pulmonary disease (COPD).

25. The method, according to claim 13, wherein Y is OH, provide that $CR^1R^2$ is not $CH_2$ and/or $NB_2$ is not $NH_2$, $N(Ph)H$, $N(Ph)CH_3$, $N(C_6H_{11})CH_3$, or $N(4-methoxybenzyl)_2$.

26. The method, according to claim 13, wherein Y is NHOH.

27. The method, according to claim 13, wherein X is $SO_2$.

28. The method, according to claim 13, wherein $R^3$ is selected from the group consisting of $C_{1-6}$ alkyl, $C_{2-6}$ alkenyl-$R^5$, halogen, CN, $NO_2$, $N(R^4)_2$, $OR^4$, $COR^4$, $NR^4R^5$, $S(O)_{0-2}R^6$, and $SO_2N(R^4)_2$.

29. The method, according to claim 13, wherein $R^7$ is selected from the group consisting of $CON(R^4)_2$, $NR^4R^5$, $SO_2N(R^4)_2$, and cycloimidyl.

30. The method, according to claim 13, wherein $R^1$ is selected from the group consisting of substituted or unsubstituted $C_{1-6}$ alkyl, $C_{1-6}$ alkyl-heteroaryl, and $C_{1-6}$ alkyl-heterocycloalkyl.

31. The method, according to claim 13, wherein $CR^1R^2$ is substituted or unsubstituted cycloalkyl or heterocycloalkyl.

32. The method, according to claim 13, wherein independently each B is selected from the group consisting of substituted or unsubstituted alkyl, cycloalkyl, heterocycloalkyl, $C_{1-6}$ alkyl-aryl, and $C_{14}$ alkyl-heteroaryl.

33. The method, according to claim 13, wherein B—N—B is substituted or unsubstituted heterocycloalkyl substituted or unsubstituted with =$NOR^4$.

34. The method, according to claim 13, wherein said compound is selected from the group consisting of methyl 2-((2-phenoxyethylsulfamoyl)methyl)-5-(3,4,4-trimethyl-2,5-dioxoimidazolidin-1-yl)pentanoate,
  methyl 2-((N-methyl-(2-phenoxyethyl)sulfamoyl)methyl)-5-(3,4,4-trimethyl-2,5-dioxoimidazolidin-1-yl)pentanoate,
  methyl 2-((N-methyl-(2-(4-chlorophenyl)ethyl)sulfamoyl)methyl)-5-(3,4,4-trimethyl-2,5-dioxoimidazolidin-1-yl)pentanoate,
  tert-butyl 2-((N-methyl-(benzofuran-2-yl)methylsulfamoyl)methyl)-5-(3,4,4-trimethyl-2,5-dioxoimidazolidin-1-yl)pentanoate,
  2-((2-phenoxyethylsulfamoyl)methyl)-5-(3,4,4-trimethyl-2,5-dioxoimidazolidin-1-yl)pentanoic acid,
  2-((N-methyl-N-(2-(4-chlorophenoxy)ethyl)sulfamoyl)methyl)-5-(3,4,4-trimethyl-2,5-dioxoimidazolidin-1-yl)pentanoic acid,
  2-((N-methyl-(benzofuran-2-yl)methylsulfamoyl)methyl)-5-(3,4,4-trimethyl-2,5-dioxoimidazolidin-1-yl)pentanoic acid,
  2-((2-phenoxyethylsulfamoyl)methyl)-5-(3,4,4-trimethyl-2,5-dioxoimidazolidin-1-yl)pentanoic acid N-hydroxy amide,
  2-((N-methyl-(2-phenoxyethyl)sulfamoyl)methyl)-5-(3,4,4-trimethyl-2,5-dioxoimidazolidin-1-yl)pentanoic acid N-hydroxy amide,
  2-((N-methyl-(2-(4-chlorophenoxy)ethyl)sulfamoyl)methyl)-5-(3,4,4-trimethyl-2,5-dioxoimidazolidin-1-yl)pentanoic acid N-hydroxy amide, and
  2-((N-methyl-(benzofuran-2-yl)methyl-sulfamoyl)methyl)-5-(3,4,4-trimethyl-2,5-dioxoimidazolidin-1-yl)pentanoic acid N-hydroxy amide.

35. The method, according to claim 13, wherein the compound is selected from the group consisting of:
  ethyl 4-(4-(4-Chlorophenyl)piperazin-1-yl)sulfonylmethyl)-tetrahydropyran-4-carboxylate,
  ethyl 4-(4-pyridyloxypiperidin-1-yl)sulfonylmethyl-tetrahydropyran-4-carboxylate,
  ethyl 4-(4-(4-Cyanophenoxy)piperidin-1-yl)sulfonylmethyl-tetrahydropyran-4-carboxylate,
  ethyl 4-(N-(2-(4-Chlorophenoxy)ethyl)-N-methylsulfamoyl-methyl)tetrahydropyran-4-carboxylate,
  ethyl 4-(4-(4-Chlorophenoxy)piperidin-1-yl)sulfonylmethyl-tetrahydropyran-4-carboxylate,
  tert-Butyl 2-(N-(2-(4-Chlorophenoxy)ethyl)-N-methyl-sulfamoylmethyl)-3-methylbutanoate,
  tert-Butyl 2-[N-Methyl-N-(2-(4-Chlorophenoxy)-2,2-dimethylethyl)sulfamoyl]methyl-3-methylbutanoate,
  tert-Butyl 2-(4-(4-Cyanophenoxyimino)piperidine-1-sulfonylmethyl)-5-(3,4,4-trimethyl-2,5-dioxoimidazolidin-1-yl)pentanoate,
  tert-Butyl 2-(4-(4-Cyanophenoxyimino)piperidin-1-ylsulfonylmethyl)-3-methylbutanoic Acid,
  tert-Butyl 2-(4-(4-Chlorobenzyloxyimino)piperidin-1-ylsulfonylmethyl)-3-methylbutanoate,
  2-((N-Methyl-N-(2-phenoxyethyl)sulfamoyl)methyl)-5-(3,4,4-trimethyl-2,5-dioxoimidazolidin-1-yl)pentanoic acid,
  4-(4-(4-Chlorophenyl)piperazin-1-yl)sulfonylmethyl)-tetrahydropyran-4-carboxylic acid,
  4-(4-Pyridyloxypiperidin-1-yl)sulfonylmethyl)-tetrahydropyran-4-carboxylic acid,
  4-(4-(4-Cyanophenoxy)piperidin-1-yl)sulfonylmethyl-tetrahydropyran-4-carboxylic acid,
  4-(N-(2-(4-Chlorophenoxy)ethyl)-N-methylsulfamoyl-methyl)tetrahydropyran-4-carboxylic acid,
  4(4-(4-Chlorophenoxy)piperidin-1-yl)sulfonylmethyl-tetrahydroxypyran-4-carboxylic Acid,
  2-(N-(2-(4-Chlorophenoxy)ethyl)-N-methylsulfamoyl-methyl)-3-methylbutanoic Acid,
  2-(N-Methyl-N-(2-(4-chlorophenoxy)-2,2-dimethylethyl)-sulfamoylmethyl)-3-methylbutanoic Acid,
  2-(4-(4-Cyanophenoxyimino)piperidin-1-ylsulfonylmethyl)-5-(3,4,4-trimethyl-2,5-dioxoimidazolidin-1-yl)pentanoic Acid, 2-(4-(4-Cyanophenoxyimino)piperidin-1-ylsulfonylmethyl)-3-methylbutanoic Acid, 2-(4-(4-Chlorobenzyloxyimino)piperidin-1-ylsulfonylmethyl)-3-methylbutanoic Acid, 2-(N-Methyl-N-(2-(4-chlorophenoxy)ethyl)-sulfamoylmethyl)-3-methylbutanoic Acid N-Hydroxy Amide, 2-(N-Methyl-N-(2-(4-chlorophenoxy)-2,2-dimethylethyl)sulfamoylmethyl)-3-methylbutanoic Acid N-Hydroxy Amide, 4-(4-(4-Pyridyloxy)piperidin-1-yl)sulfonylmethyl)-tetrahydropyran-4-carboxylic Acid N-Hydroxy Amide Hydrochloride, 4-(4-(4-Cyanophenoxy)piperidin-1-yl)sulfonylmethyl-tetrahydropyran-4-carboxylic Acid N-Hydroxy Amide, 4-(N-(2-(4-Chlorophenoxy)ethyl)-N-methylsulfamoylmethyl)tetrahydropyran-4-carboxylic Acid N-Hydroxy Amide, 4-(4-(4-Chlorophenoxy)piperidin-1-yl)sulfonylmethyl-tetrahydropyran-4-carboxylic Acid N-Hydroxy Amide, 2-[4-(4-Cyanophenoxyimino)piperidin-1-ylsulfonylmethyl]-5-(3,4,4-trimethyl-2,5-dioxoimidazolidin-1-yl)pentanoic Acid N-Hydroxy Amide, 2-(4-(4-Cyanophenoxyimino)piperidin-1-ylsulfonylmethyl)-3-methylbutanoic Acid N-Hydroxy Amide, 2-(4-(4-Chlorobenzyloxyimino)piperidin1-ylsulfonylmethyl)-3-methylbutanoic Acid N-Hydroxy Amide, 2-((N-Ethyl-N-(2-methoxyethyl)-sulfamoylmethyl)-5-(3,4,4-trimethyl-2,5-dioxoimidazolidin-1-yl)-pentanoic Acid N-Hydroxy Amide, 2-(3,3-Diphenylpropylsulfamoylmethyl)-5-(3,4,4-trimethyl-2,5-dioxo-imidazolidin-1-yl)-pentanoic Acid N-Hydroxy Amide, 2-(Cyclohexylmethylsulfamoylmethyl)-5-(3,4,4-trimethyl-2,5-dioxoimidazolidin-1-yl)-pentanoic Acid N-Hydroxy Amide, 2-(1-Methyl-3-phenylpropylsulfamoylmethyl)-5-(3,4,4-trimethyl-2,5-dioxoimidazolidin-1-yl)pentanoic Acid N-Hydroxy Amide, 2-((3-Phenylpropyl)sulfamoylmethyl)-5-(3,4,4-trimethyl-2,5-dioxo-imidazolidin-1-yl)-pentanoic Acid N-Hydroxy Amide, 2-((N-Methyl-N-octylsulfamoyl)methyl)-5-(3,4,4-trimethyl-2,5-dioxoimidazolidin-1-yl)-pentanoic Acid N-Hydroxy Amide, 2-(N-(2-Cyanoethyl)-N-octylsulfamoylmethyl)-5-(3,4,4-trimethyl-2,5-dioxoimidazolidin-1-yl)-pentanoic Acid N-Hydroxy Amide, 2-(N-(2-(4-Chlorophenoxy)-1-methylethyl)-N-methylsulfamoylmethyl)-5-(3,4,4-trimethyl-2,5-dioxo-imidazolidin-1-yl)-pentanoic Acid N-Hydroxy Amide, 2-(N-methyl-N-phenethylsulfamoylmethyl)-5-(3,4,4-trimethyl-2,5-dioxoimidazolidin-1-yl)-pentanoic Acid N-Hydroxy Amide, 2-(N-(2-(2-Chlorophenoxy)ethyl)-N-methyl-sulfamoylmethyl)-5-(3,4,4-trimethyl-2,5-dioxoimidazolidin-1-yl)-pentanoic Acid N-Hydroxy Amide, 2-(N-Ethyl-N-phenylsulfamoylmethyl)-5-(3,4,4-trimethyl-2,5-dioxo-imidazolidin-1-yl)-pentanoic Acid N-Hydroxy Amide, and 2-(N-(4-Chlorophenyl)-N-methylsulfamoylmethyl)-5-(3,4,4-trimethyl-2,5-dioxoimidazolidin-1-yl)pentanoic Acid N-Hydroxy Amide.

* * * * *

UNITED STATES PATENT AND TRADEMARK OFFICE
CERTIFICATE OF CORRECTION

PATENT NO. : 6,187,924
DATED : February 13, 2001
INVENTOR(S) : Baxter et al.

It is certified that error appears in the above-identified patent and that said Letters Patent is hereby corrected as shown below:

Column 28, line 26 (Claim 1): "$SO_{2-2}R6$," should read --$SO_{0-2}R6$,--.

Column 30, line 63 (Claim 10): "dioxoimidazolidin-lyl)-" should read --dioxoimidazolidin-1-yl)- --.

Column 31, line 15 (Claim 10):"dioxoimidazolidin-lyl)" should read --dioxoimidazolidin-1-yl)--.

Column 32, line 29 (Claim 13): :$SO_{0-2}R^6$ $CO_2R^6$" should read --$SO_{0-2}R^6$,$CO_2R^6$--.

Column 33, line 29 (Claim 25): "provide" should read --provided--.

Signed and Sealed this

Fifth Day of June, 2001

Attest:

Attesting Officer

NICHOLAS P. GODICI
*Acting Director of the United States Patent and Trademark Office*